US011925681B2

(12) United States Patent
Morici et al.

(10) Patent No.: US 11,925,681 B2
(45) **Date of Patent: *Mar. 12, 2024**

(54) BURKHOLDERIA PSEUDOMALLEI COMPLEX OUTER MEMBRANE VESICLES AS ADJUVANTS

(71) Applicant: Administrators of the Tulane Educational Fund, New Orleans, LA (US)

(72) Inventors: Lisa Ann Morici, Mandeville, LA (US); James B. McLachlan, New Orleans, LA (US); Christopher J. H. Davitt, Medford, MA (US); Jonathan R. Kurtz, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/088,690

(22) Filed: Dec. 26, 2022

(65) Prior Publication Data

US 2023/0146032 A1 May 11, 2023

Related U.S. Application Data

(63) Continuation of application No. 17/046,723, filed as application No. PCT/US2019/026769 on Apr. 10, 2019, now Pat. No. 11,534,486.

(60) Provisional application No. 62/655,667, filed on Apr. 10, 2018.

(51) Int. Cl.

| | |
|---|---|
| ***A61K 39/02*** | (2006.01) |
| ***A61K 39/00*** | (2006.01) |
| ***A61K 39/12*** | (2006.01) |

(52) U.S. Cl.

CPC .......... *A61K 39/02* (2013.01); *A61K 39/0002* (2013.01); *A61K 39/12* (2013.01); *A61K 2039/5254* (2013.01)

(58) Field of Classification Search

None

See application file for complete search history.

(56) References Cited

U.S. PATENT DOCUMENTS

| | | | | |
|---|---|---|---|---|
| 9,526,775 B2 | 12/2016 | Feldman | | |
| 10,639,280 B2 | 5/2020 | Salverda | | |
| 11,066,453 B2 | 7/2021 | Grandi | | |
| 11,534,486 B2 * | 12/2022 | Morici | .................. | A61K 39/02 |
| 2014/0004178 A1 * | 1/2014 | Morici | ................. | A61K 39/104 424/234.1 |
| 2015/0118263 A1 * | 4/2015 | Feldman | ................. | A61P 31/04 435/317.1 |
| 2017/0333543 A1 | 11/2017 | Torres | | |

FOREIGN PATENT DOCUMENTS

| | | |
|---|---|---|
| WO | WO 2003/051379 A1 | 6/2003 |
| WO | WO 2010/036938 A2 | 4/2010 |
| WO | WO 2012/097185 A2 | 7/2012 |

OTHER PUBLICATIONS

Shi, S., et al., Vaccine adjuvants: Understanding the structure and mechanism of adjuvanticity, Vaccine, 2019, p. 3167-3178.

Baker, SM, A Burkholderia pseudomallei Outer Membrane Vesicle Vaccine Provides Cross Protection Against Inhalational Glanders, Vaccines, Dec. 9, 2017, pp. 1-17, v. 5(4).

Chen, DJ, et al., Delivery of foreign antigens by engineered outer membrane vesicles, Proc Natl Acad Sci USA, Feb. 16, 2017, epub Jan. 2017, pp. 3099-3104, v. 107(7).

Petersen, H., et al., Evaluation of a Burkholderia pseudomallei Outer Membrane Vaccine in Nonhuman Primates, Procedia Vaccinol., Jan. 1, 2014, pp. 38-42, v. 8.

Thomas, S., Intl Search Report, ISA/US, PCT/US19/26769, dated Jul. 18, 2019.

Thomas, S., Written Opinion, ISA/US, PCT/US19/26769, dated Jul. 18, 2019.

Nieves, W., et al., A naturally derived outer-membrane vesicle vaccine protects agains lethal pulmonary Burkholderia pseudomallei infection, 2011, pp. 8381-8389, v. 29.

Fateh, A., et al., New insight into the application of outer membrane vesicles of Gram-negative bacteria, Vaccine Res., Aug. 11, 2015, 93-9, v. 2(5).

Tuanyok, A., et al., Burkholderia humptydooensis sp. nov., a new species related to Burkholderia thailandensis and ... , App and Environ Microbiol, Mar. 2017, pp1-10, v 83(5).

Godoy, D., et al., Multilocus Sequence Typing and Evolutionary Relationships among the causative agents of Meliodosis ... , J Clin Microbiol, May 2003, pp. 2068-2079, v. 41(5).

Hall, C., et al., Expanding the Burkholderia pseudomallei Complex with the addition of two novel species: Burkholderia, App. and Environ Microbiol, Jan. 2022, pp. 1-12, v 88(1).

* cited by examiner

*Primary Examiner* — Jennifer E Graser

(74) *Attorney, Agent, or Firm* — Laurence J. Hyman; Hyman IP Law

(57) ABSTRACT

Outer membrane vesicles from bacteria of the *Burkholderia pseudomallei* complex can be used as adjuvants in compositions and methods to potentiate the immune response to immunogens.

35 Claims, 16 Drawing Sheets

A

B

BURKHOLDERIA PSEUDOMALLEI COMPLEX OUTER MEMBRANE VESICLES AS ADJUVANTS

CROSS-REFERENCE TO RELATED APPLICATIONS

This application is a continuation of U.S. patent application Ser. No. 17/046,723, filed Oct. 9, 2020, which is a national stage application under 35 U.S.C. § 371 of International Application No. PCT/US19/026769, filed Apr. 19, 2010, which claimed priority to, and the benefit of, U.S. Provisional Patent Application No. 62/655,667, filed Apr. 10, 2018. This application claims priority to, and the benefit of, each of the applications identified above, the contents of which are incorporated herein by reference for all purposes.

STATEMENT OF FEDERAL FUNDING

Not applicable.

BACKGROUND OF THE INVENTION

Vaccines are a cost-effective medical intervention, and one of the great advances in promoting human health. Unfortunately, many vaccines suffer from weak or limited immunogenicity. This is particularly true for killed organism vaccines and for sub-unit vaccines, which are generally poor inducers of adaptive immunity and generate a primarily humoral response, with little induction of cell-mediated activity. See, e.g., Lee and Nguyen, "Recent Advances of Vaccine Adjuvants for Infectious Diseases," Immune Network, 2015, 15(2):51-57, doi.org/10.4110/in.2015.15.2.51; Schijns and Lavelle, Trends in vaccine adjuvants, Expert Review of Vaccines, 2014, 10:4, 539-550, DOI: 10.1586/erv.11.21. The immunogenicity of vaccines can be enhanced by use of adjuvants, substances which enhance a subject's immune response to a vaccine. Unfortunately, many substances that strongly increase immune response in animals, such as Freund's Complete Adjuvant, are also toxic and only a few adjuvants have been approved for use in humans. The most commonly used adjuvant is "alum," which denotes any of several aluminum salts that are used as an adjuvant in over 80% of currently approved vaccines. Unfortunately, alum adjuvants tend to enhance humoral (antibody) responses but are poor inducers of cell-mediated responses.

Gram-negative bacteria secrete outer membrane vesicles ("OMVs"), which are sections of outer membrane which separate from the cell and encapsulate of portion of periplasmic space Klimentova and Stulik, "Methods of isolation and purification of outer membrane vesicles from gram-negative bacteria," Microbiological Res, 2015, 170:1-9, doi.org/10.1016/j.micres.2014.09.006. OMVs contain constituents of the outer membrane, such as lipopolysaccharide, phospholipids and proteins, and may contain virulence factors and other cytosolic proteins. Id. OMVs of meningococcus have been explored as adjuvants for meningococcal vaccines since at least 2011 (e.g., Sanders and Feavers, "Adjuvant properties of meningococcal outer membrane vesicles and the use of adjuvants in *Neisseria meningitidis* protein vaccines," Expert Rev Vaccines. 2011 March; 10(3): 323-34. doi: 10.1586/erv.11.10). A report in 2014 showed meningococcus engineered to produce OMVs with a less toxic form of lipopolysaccharide enhanced immune response to both meningococcal antigens and to tetanus toxoid. Nagaputra et al., "*Neisseria meningitides* Native Outer Membrane Vesicles Containing Different Lipopolysaccharide Glycoforms as Adjuvants for Meningococcal and Nonmeningococcal Antigens," Clin. Vaccine Immunol., 2014, 21(2):234-242.

OMVs of the gram-negative intracellular *bacillus Burkholderia pseudomallei* used as a vaccine provide significant protection against pneumonic melioidosis, a disease caused by that organism, and were recently shown to also provide significant protection against glanders, caused by the closely related *bacillus B. mallei*. Baker, et al., A *Burkholderia pseudomallei* Outer Membrane Vesicle Vaccine Provides Cross Protection against Inhalational Glanders in Mice and Non-Human Primates," Vaccines, 2017, 5:49, doi:10.3390/vaccines5040049 (hereafter, sometimes referred to as "Baker 2017").

A need remains in the art for adjuvants which can elicit enhanced cell-mediated immunity and humoral responses to immunogens derived from heterologous pathologic organisms or from cancer cells. Surprisingly, the invention fills these and other needs.

SUMMARY OF THE INVENTION

In a first group of embodiments, the invention provides immunogenic compositions comprising (a) a non-Burkhorlderia immunogen and (b) a plurality of outer membrane vesicles (OMVs) derived from one or more organisms of the species *Burkholderia pseudomallei, B. mallei, B. oklahomensis, B. thailandensis, B. humptydooensis*, or *Burkholderia* spp. Clades A, B, or C (collectively, the "*B. pseudomallei* complex" or "Bpc"). In some embodiments, the *Burkholderia* species is *B. pseudomallei* or *B. mallei*. In some embodiments, the Bpc species has attenuated pathogenicity compared to wild-type members of the Bpc species. In some embodiments, the attenuated pathogenicity of said Bpc species is due to deletion or truncation of purM. In some embodiments, the Bpc species is *B. pseudomallei*. In some embodiments, the attenuated pathogenicity is due to deletion or disruption of tonB, of hcp1, or of both of said wild-type Bpc species. In some embodiments, the composition further comprises an aluminum salt, saponin, oil-in-water, or CpG nucleotide adjuvant. In some embodiments, the composition further comprises a pharmaceutically acceptable excipient. In some embodiments, the immunogen is a killed or attenuated pathogenic organism or is derived from a pathogenic organism. In some embodiments, the killed or attenuated pathogenic organism or the pathogenic organism from which said immunogen is derived, is a bacterium. In some embodiments, the bacterium is a *Bacillus, Rickettsia, Chlamydia, Chlamydophila, Mycobacteria, Salmonella, Shigella, Spirochete, Listeria*, or *Mycoplasma*. In some embodiments, the bacterium is *Mycobacterium tuberculosis* or *Bacillus anthracis*. In some embodiments, the killed or attenuated pathogenic organism or the pathogenic organism from which said immunogen is derived, is a virus. In some embodiments, the virus is a rabies virus, herpes simplex virus type 2, herpes simplex virus type 1, human cytomegalovirus, Epstein-Barr virus, varicella zoster virus, human papillomavirus, Human T-cell lymphotropic virus type 1, rotavirus, norovirus, hepatitis A virus, hepatitis B virus, hepatitis C virus, influenza virus, polio virus, Japanese encephalitis virus, measles virus, mumps virus, rubella virus, yellow fever virus, varicella virus, dengue virus, hantavirus, human immunodeficiency virus-1, Ebola virus, Marburg virus, Lassa virus, Lymphocytic choriomeningitis virus, Nipah virus, Rift Valley fever virus, Middle East Respiratory Syndrome Coronavirus, SARS coronavirus, Crimean-Congo hemorrhagic fever virus, Zika virus, or West Nile virus. In some embodiments, the killed or attenuated pathogenic organism or the pathogenic organism from which said immunogen is derived, is a fungus. In some embodiments, the fungus is an *Aspergillus, Pneumocystis, Histoplasma, Coccidioides, Malassezia, Blastomyces*, or *Candida* fungus. In some embodiments, the killed or attenuated pathogenic organism or the pathogenic organism from which said immunogen is derived, is a parasite. In some embodiments, the parasite is a *Plasmodium*, a *Schistosoma*, a *Leishmania*, a helminth, or a *Trypanosoma*. In some embodiments, the immunogen is derived from a cancer cell. In some embodiments, the immunogen derived from a cancer cell is an activated oncogene, a fetal antigen, an activation marker, an overexpressed growth factor, or a neoantigen. In some embodiments, the cancer cell is a cell of a lymphoma, a leukemia, a prostate cancer, a breast cancer, a pancreatic cancer, a small cell lung cancer, a non-small cell lung cancer, a colon or rectal cancer, a liposarcoma, a melanoma, a bladder cancer, a liver or intrahepatic duct cancer, an endometrial cancer, or an ovarian cancer. In some embodiments, the immunogen is encapsulated within the OMV. In some embodiments, the immunogenic composition further comprises a stabilizer, a buffer, or both a stabilizer and a buffer. In some embodiments, the immunogen is an opioid drug.

In a second group of embodiments, the invention provides methods of increasing a subject's immune response to a non-*Burkholderia* immunogen, comprising co-administering to the subject (a) an effective amount the immunogen and (b) an effective amount of outer membrane vesicles (OMVs) of one or more species selected from the group consisting of *Burkholderia pseudomallei, B. mallei, B. oklahomensis, B. thailandensis, B. humptydooensis, Burkholderia* spp. Clade A, *Burkholderia* spp. Clade B, and *Burkholderia* spp. Clade C (collectively, "*B. pseudomallei* complex" or "Bpc"). In some embodiments, the immunogen and the effective amount of said OMVs are in a single composition. In some embodiments, the composition is lyophilized. In some embodiments, the lyophilized composition is reconstituted prior to the co-administration. In some embodiments, the composition further comprises a stabilizer, a buffer, or both a stabilizer and a buffer. In some embodiments, the subject is a primate, an equine, a bovine, an ovine, a porcine, a canine, a feline, or a camelid. In some embodiments, the primate is a human. In some embodiments, the OMVs are of *B. pseudomallei* or *B. mallei*. In some embodiments, the *Burkholderia pseudomallei, B. mallei, B. oklahomensis, B. thailandensis, B. humptydooensis, Burkholderia* spp. Clade A, *Burkholderia* spp. Clade B, or *Burkholderia* spp. Clade C, respectively, have attenuated pathogenicity compared to wild type *Burkholderia pseudomallei, B. mallei, B. oklahomensis, B. thailandensis, B. humptydooensis, Burkholderia* spp. Clade A, *Burkholderia* spp. Clade B, or *Burkholderia* spp. Clade C, respectively. In some embodiments, the attenuated pathogenicity is due to deletion or truncation of purM or of deletion or disruption of tonB, of hcp1, or of both. In some embodiments, the *B. pseudomallei* is *B. pseudomallei* Bp82. In some embodiments, the immunogen is derived from a pathogenic organism. In some embodiments, the killed or attenuated pathogenic organism or the pathogenic organism from which said immunogen is derived, is a bacterium. In some embodiments, the bacterium is a *Bacillus, Rickettsia, Chlamydia, Chlamydophila, Mycobacteria, Salmonella, Shigella, Spirochete, Listeria*, or *Mycoplasma*. In some embodiments, the bacterium is *Mycobacterium tuberculosis* or *Bacillus anthracis*. In some embodiments, the killed or attenuated pathogenic organism or the pathogenic organism from which said immunogen is derived is a virus. In some embodiments, the virus is a herpes simplex virus type 2, herpes simplex virus type 1, human cytomegalovirus, Epstein-Barr virus, varicella zoster virus, human papillomavirus, Human T-cell lymphotropic virus type 1, rabies virus, rotavirus, norovirus, hepatitis A virus, hepatitis B virus, hepatitis C virus, influenza virus, polio virus, Japanese encephalitis virus, measles virus, mumps virus, rubella virus, yellow fever virus, varicella virus, dengue virus, hantavirus, human immunodeficiency virus-1, Ebola virus, Marburg virus, Lassa virus, Lymphocytic choriomeningitis virus, Nipah virus, Rift Valley fever virus, Middle East Respiratory Syndrome Coronavirus, SARS coronavirus, Crimean-Congo hemorrhagic fever virus, Zika virus, or West Nile virus. In some embodiments, the killed or attenuated pathogenic organism or the pathogenic organism from which said immunogen is derived is a fungus. In some embodiments, the fungus is an *Aspergillus, Pneumocystis, Histoplasma, Coccidioides, Malassezia, Blastomyces*, or *Candida* fungus. In some embodiments, the immunogen is derived from a cancer cell. In some embodiments, the cancer cell is a cell of a lymphoma, a leukemia, a prostate cancer, a breast cancer, a pancreatic cancer, a small cell lung cancer, a non-small cell lung cancer, a colon or rectal cancer, a liposarcoma, a melanoma, a bladder cancer, a liver or intrahepatic duct cancer, an endometrial cancer, or an ovarian cancer. In some embodiments, the immunogen derived from said cancer cell is an activated oncogene, a fetal antigen, an activation marker, an overexpressed growth factor, or a neoantigen. In some embodiments, the immunogen is an opioid drug. In some embodiments, the co-administration is intravenous, intraperitoneal, intramuscular, intracavity, subcutaneous, intradermal, intranasal, or transdermal.

BRIEF DESCRIPTION OF THE DRAWINGS

FIGS. 10A and 10B are graphs showing that *Burkholderia* outer membrane vesicles (BOMV) augment cell responses during vaccination. FIG. 10A presents the results with respect to CD4 T cells, while FIG. 10B presents the results with respect to CD8 T cells. To the right of the graphs are representative flow plots of the results for CD4 T cells and for CD8 T cells, respectively. Total antigen-specific T cell numbers were calculated and compared using One-Way ANOVA (n=4 per group *, $p<0.05$; **, $p<0.01$).

CD4 T cell responses in mice injected subcutaneously with a prime-boost regimen using OMVs as an adjuvant.

Figure 12:
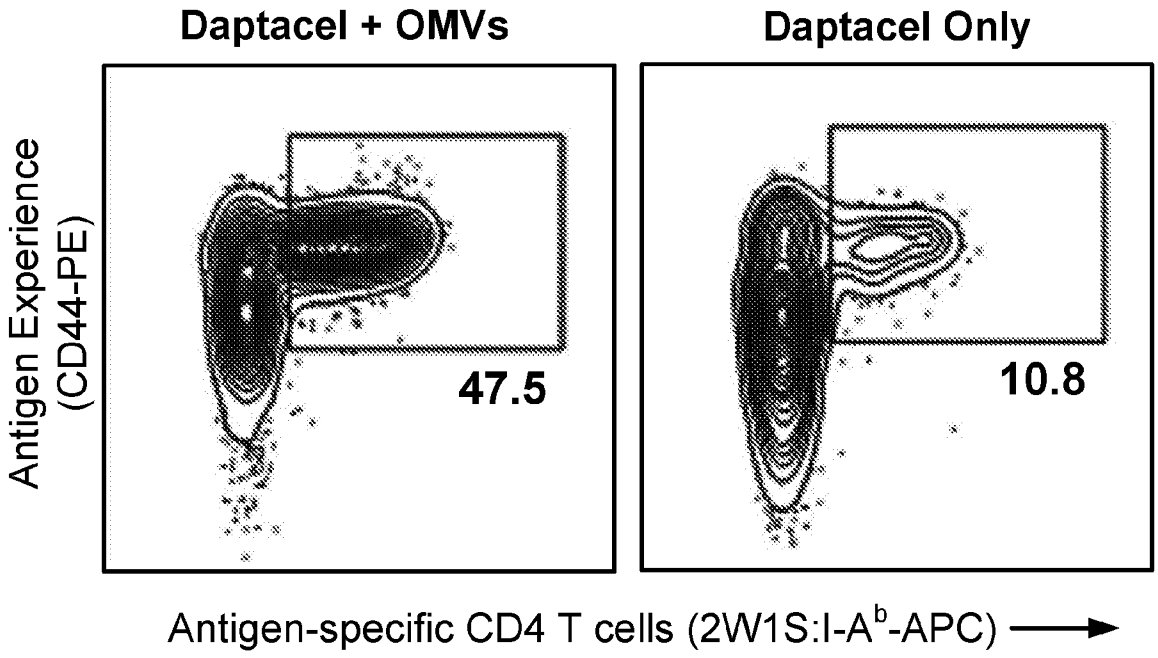

FIG. 12 presents representative flow plots comparing the adjuvant effect of *Burkholderia* outer membrane vesicles (OMVs) administered with DAPTACEL® (left hand plot) to the effect of DAPTACEL® alone (right hand plot) in a non-human primate ("NHP") model.

Figure 13:
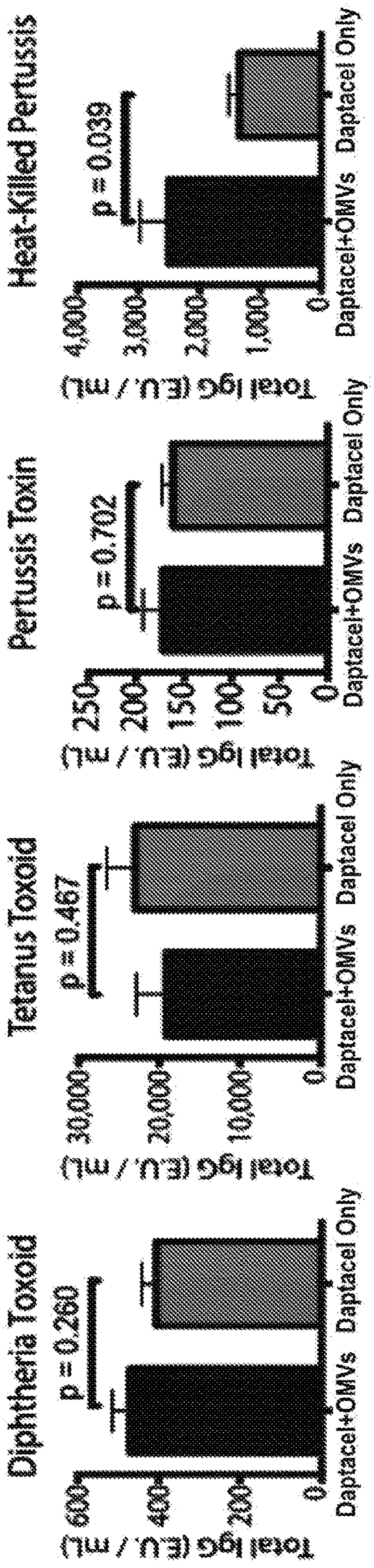

FIG. 13 presents a series of graphs comparing antibody responses to the individual antigens in DAPTACEL® DTaP vaccine in mice inoculated intradermally with either the vaccine alone or with the vaccine plus 1 μg Bp82 outer membrane vesicles (OMVs) on day 0 and then boosted on day 14. Groups were compared using a Student's t test (n=5-9 mice per group).

Figure 14:
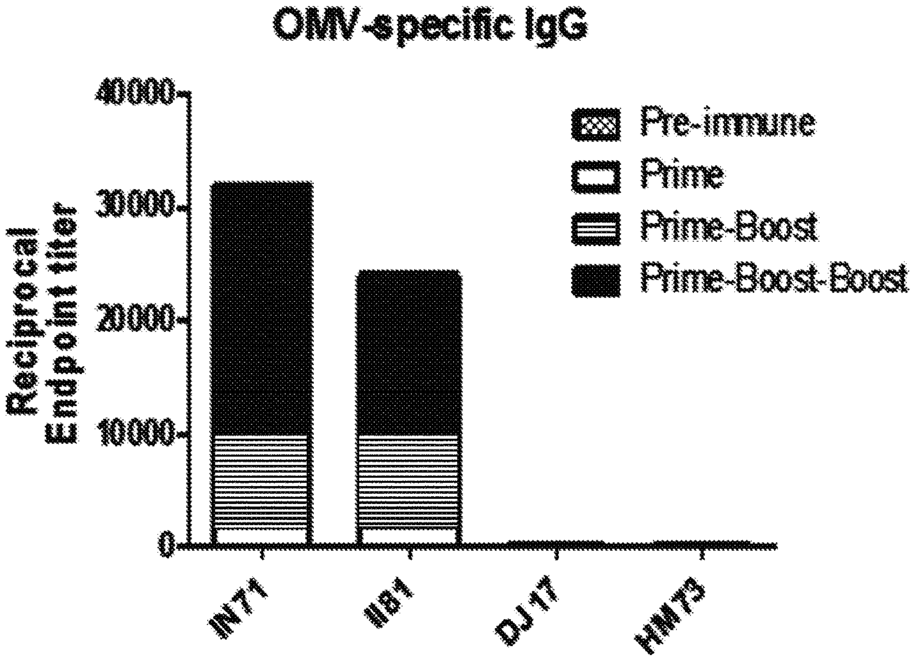

FIG. 14 is a graph showing that immunization of Rhesus macaques with the exemplar Bpc OMVs induces an IgG response. IN71 and 1181 denote macaques that were immunized with Bpc OMVs ("OMV"), while DJ17 and HM73 denote macaques that were given sham injections as controls. Each animal was immunized three times, with each immunization a month from the prior one. Blood was collected two weeks after each immunization and serum IgG was measured by ELISA.

Figure 15:
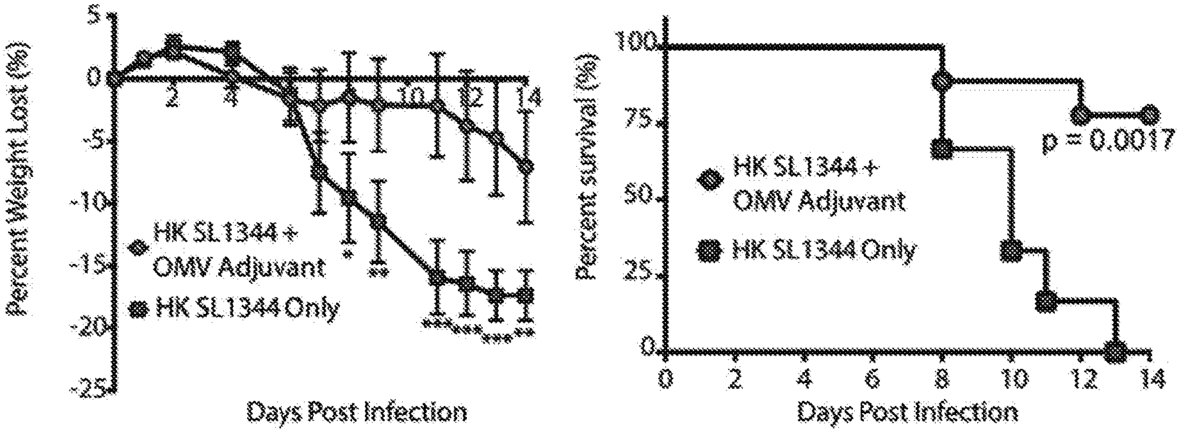

FIG. 15 presents two graphs regarding the response of mice challenged on day 28 by oral administration of $1\times10^5$ CFUs of wild-type S. *Typhimurium* SL1344 ("HK SL 1344") to mice that had first been immunized on day 0 and day 14 with $3\times10^8$ CFUS of heat killed S. *Typhimurium* SL1344 ("HK SL 1344") either with or without 10 μg of Bp82 OMVs ("OMV Adjuvant"). The left hand graph shows the percent of weight loss of the mice in the respective groups, monitored daily, over the days following the challenge dose. Animals were humanely euthanized when they lost >20% of their prechallenge weight. The right hand graph shows the percent survival of the respective groups of mice on the days following the challenge dose. Mouse weight was statistically analyzed using multiple Student t tests, comparing each group per day (n=6-9 mice per group; *, $p<0.05$; , $p<0.01$; *, $p<0.001$). Mouse survival was analyzed using a Mantel-Cox test (n=6-9 mice per group)

Figure 16A:
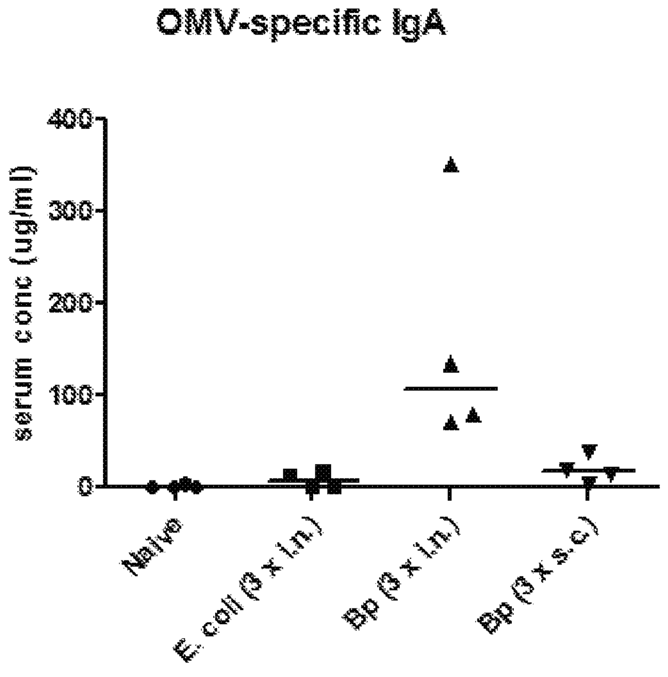
Figure 16B:
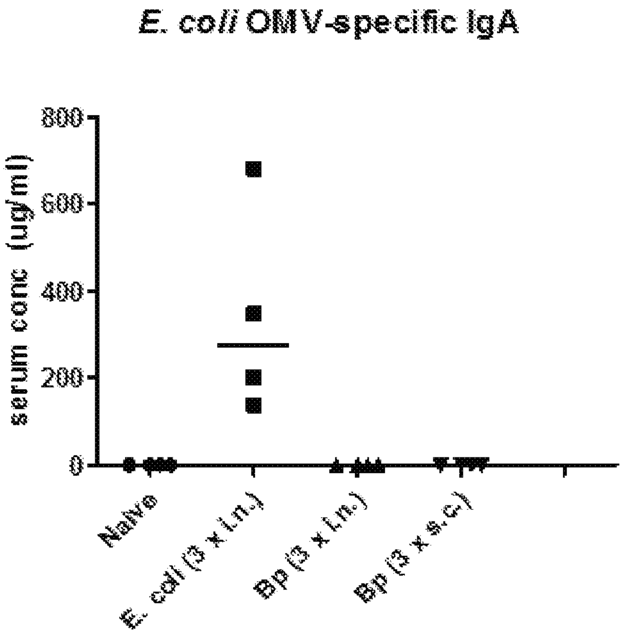

FIGS. 16A and 16B. FIG. 16A shows the serum concentration of IgA specific for Bpc outer membrane vesicles ("OMV") measured by ELISA in serum from mice treated by different regimens, while FIG. 16B shows the serum concentration of IgA specific for *E. coli* outer membrane vesicles ("*E. coli* OMV") measured by ELISA in serum from mice administered OMVs as designated. Both Figures: Naïve=non-treated mice (controls). Ec IN=mice administered *E. coli* OMV-immunized intranasally. Bp IN: mice administered Bpc OMVs intranasally. Bp SC: mice administered Bpc OMVs subcutaneously. Horizontal line represents the median value for each group (n=5) (*$P<0.05$, $P<0.01$, *$P<0.001$ using a one-way ANOVA with Bonferroni's post-test).

Figure 17:
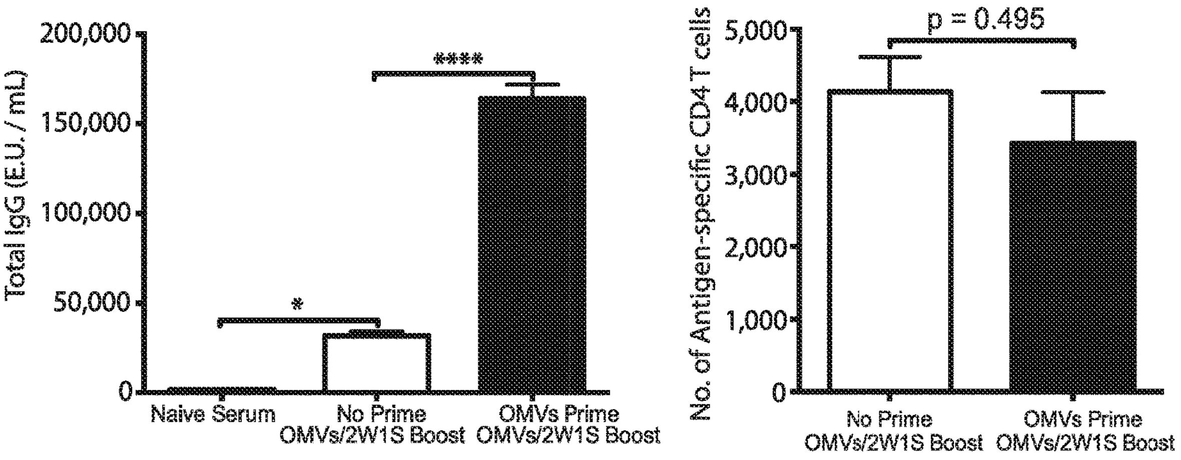

FIG. 17 presents two graphs showing that pre-existing antibodies to outer membrane vesicles ("OMV") from an exemplar member of the Bpc do not inhibit the ability of the OMVs to act as adjuvants. Left hand graph: Y axis shows total IgG measured by E.U./mL. Y axis: "Naïve serum"=serum from mice not immunized with OMV. Right hand graph: Y axis shows number of antigen-specific CD4 T cells. X axis of both graphs: "No prime OMVs/2W1S Boost"=serum from mice given phosphate buffered saline on days 0 and 7 and then 1 μg of Bp82 OMVs and 200 ng of a T cell antigen, 2W1S peptide. "OMVs Prime OMVs/2W1S Boost": serum from mice administered 1 μg of Bp82 OMVs subcutaneously on days 0 and 7 and then with 1 μg of Bp82 OMVs and 200 ng of 2W1S peptide on days 14 and 21.

DETAILED DESCRIPTION

Surprisingly, we have now found that outer membrane vesicles ("OMVs") from *Burkholderia pseudomallei* (*B. pseudomallei*, sometimes referred to herein as "Bp"), a gram-negative *bacillus*, previously explored as a vaccine against meliodiosis caused by that organism or against glanders, a disease caused by the closely-related *bacillus B. mallei*, strongly enhance immune response to co-administered antigens from unrelated organisms and therefore can serve as powerful new adjuvants for enhancing the immune response of subjects to vaccines to unrelated organisms, without evident toxicity to the subject. As reported in the Examples below, OMVs from an exemplar Bp were shown to be highly effective adjuvants in enhancing immune response in animal studies. Seventy percent of mice to which Bp OMVs were orally administered with heat-killed *Salmonella* ("HKS") bacteria developed immunity that protected them when challenged with a lethal dose of live *Salmonella*, yet showed no evidence of toxicity from the OMVs. Moreover, studies in a standard insect model of toxicity showed that waxworms injected with Bp OMVs remained healthy, as shown by progression to pupation, while 70% of worms injected with *E. coli* OMVs died. Mice administered Bp OMVs orally or intranasally showed no evidence of toxicity, and mice and non-human primates injected with Bp OMVs showed no adverse reactions around the injection site.

Further, mice injected with Bp OMVs and a commercial vaccine with diphtheria, tetanus, and pertussis antigens ("DTaP") already adjuvanted with alum showed enhanced Th1 and Th17 CD4 T cell responses, without diminishing their antibody response to Diphtheria toxoid, Tetanus toxoid, or to Pertussis toxin. These surprising findings have several important implications.

First, the results demonstrate that the Bp OMVs enhanced immune response to a vaccine that was already adjuvanted with alum, the most commonly used adjuvant in vaccines for human use. This shows that Bp OMVs and, by extension, OMVs of other members of the *Burkholderia pseudomallei* complex (sometimes referred to herein as "Bpc"; the Bpc is discussed in more detail below), can be added to current, alum-adjuvanted vaccines to enhance the immune responses generated by those vaccines and, therefore, to provide better protection against the pathogens targeted by the vaccine than is provided by the current vaccines. Bpc OMVs are also expected to be useful when used in combination with other adjuvants, including oil-in-water, saponin, toll-like receptors (see, e.g., Steinhagen et al., Vaccine, 2011, 29(17): 3341-3355), or CpG deoxynucleotides (see, e.g., Bode, et al., Expert Rev Vaccines, 2011, 10(4): 499-511), to further potentiate the immune response to vaccines in which these adjuvants are used.

Second, the results demonstrate that, unlike alum, which primarily raises a humoral (antibody) response to antigens with which it is administered, the Bp OMVs surprisingly caused both CD4 and CD8 T cell responses, while not diminishing humoral responses to the vaccine. Bp OMVs should therefore be surprisingly superior adjuvants for vaccines against pathogens in which a cellular response is expected to be useful (for example, in vaccines against parasites) and suggests that Bp OMVs and, by extension, *Burkholderia pseudomallei* complex OMVs (sometimes referred to herein as "Bpc OMVs" or as "BOMVs"), can be used as adjuvants for vaccines for which alum or other current adjuvants that primarily raise humoral response do not provide an effective adjuvant response, or to further potentiate the adjuvant response provided by alum or other current adjuvants which primarily raise a humoral response.

The studies set forth below further demonstrate that exemplar Bpc OMVs were both parenterally and mucosally immunogenic, and did not raise an immune response that interfered with their ability to enhance an immune response later when administered with an antigen. Moreover, mice and non-human primates to which exemplar Bpc OMV-adjuvanted compositions were administered showed no sign of necrosis around the injection site or other signs of toxicity. Without wishing to be bound by theory, it is surmised this lack of toxicity may be due in part to an attenuation of the toxicity of *Burkholderia* lipopolysaccharide, or "LPS", compared to the LPS of some other bacterial genera, such as *Pseudomonas*. And, again without wishing to be bound by theory, it is further believed that the LPS of some other genera, including *Pseudomonas*, will change the adjuvanticity of their OMVs and polarize the direction of any immune response produced by their use. In contrast, the exemplar Bpc OMVs produced a balanced immune response. This surprisingly favorable combination of qualities such as lack of toxicity and a balanced immune response make Bpc OMVs superior adjuvants for vaccines and in methods for enhancing the immune response to vaccines by co-administering them with Bpc OMVs.

The exemplar Bpc OMVs used in the studies reported herein were OMVs derived from Bp82, a mutant in which the pathogenicity of *B. pseudomallei* strain 1026b has been attenuated by deletion of purM, as described in Propst et al., Infection and Immun, 2010, 78(7):3136-3143. One advantage of Bp82 is that, as suggested by the article, it can be used in lower level biosafety facilities than can unmodified Bp in general or Bp strain 1026b in particular. However, *Burkholderia* whose virulence is attenuated by other means can also be used for their convenience of handling and production. Torres, U.S. Patent Application Publication 2017/0333543 teaches the production of Burholderia whose pathogenicity is attenuated by deletion or disruption of the tonB and hcp1 genes, including attenuated *B. mallei*. OMVs from *Burkholderia* engineered with deletion or disruption of these genes as taught in the Torres patent publication can be used in the inventive compositions and methods.

The lab of one of the present inventors, Morici, has studied the OMVs of a different strain of Bp, *B. thailandensis*, and found them to be very similar in structure and composition to those of Bp strain 1026b. Due to this structural and compositional similarity, it is believed that OMVs derived from any strain of *B. pseudomallei* can be used in the inventive compositions and methods. While Bp OMVs are particularly preferred, it is believed that OMVs from other members of the Bpc can be used. As used herein, and as described in more detail below, the Bpc comprises *B. pseudomallei, B. mallei, B. oklahomensis, B. thailandensis, B. humptydooensis*, and three unassigned *Burkholderia* spp. Clades A (represented by type strain BDU 5), B (represented by type strain BDU 8) and C (represented by type strain MSMB0265). In some embodiments, the OMVs are from *B. thailandensis*, which is easier to work with in the lab because it is less pathogenic than other members of the Bpc.

Culturing of Bp and obtaining OMVs from species of *Burkholderia* are described in, for example, Nieves, et al., Vaccine, 2011, 29(46): 8381-8389, doi:10.1016/j.vaccine.2011. 08.058; Nieves, et al., Clin Vaccine Immunol. 2014, 21(5):747-54. doi: 10.1128/CVI. 00119-14, and Baker et al., Vaccines (Basel). 2017 December; 5(4): 49, doi:

10.3390/vaccines5040049 (hereinafter, "Baker 2017"). While OMVs from *B. mallei* can used in some embodiments of the inventive compositions and methods, it is a facultative intracellular *bacillus* and therefore harder to culture than Bp. It is expected that members of the Bpc that can be efficiently cultured outside of mammalian host cells will generally be preferred in some embodiments of the inventive compositions and methods due to the relative ease of production of OMVs.

In studies using *Burkholderia* OMVs as immunogens to raise a protective response against diseases caused by *Burkholderia* (i.e., melioidosis and glanders), a stronger protective response was seen when the organisms were grown under nutrient-deprived environmental conditions that increased the presence of type III and type VI secretion system components. Without wishing to be bound by theory, it is surmised that the increased presence of these secretion system factors were present in OMVs derived from the bacteria raised under these environmental conditions, and that the increased presence of one or more of these factors was responsible for some of the protective effect seen in using the OMVs to inoculate animals against diseases caused by the organisms. In contrast, the Bps in the present study were grown in Luria broth, which is not known to be deficient in any nutrients necessary for growth of the organism. It is therefore believed that OMVs useful for use as adjuvants can be derived from a broader group of organisms than OMVs intended for use as vaccines against melioidosis or glanders. In some preferred embodiments, the OMVs are derived from members of the Bpc that have not been environmentally stressed. In some preferred embodiments, the members of the Bpc that have not been environmentally stressed are Bp.

Adjuvants enhance the immune response to antigens when they are co-administered to a patient at the same location at the same time, or closely enough in time so that the patient's immune system components "see" the antigen and the adjuvant together. Persons of skill would not expect, for example, that BOMVs administered to one arm of a subject would enhance the subject's immune response to a vaccine separately administered to the subject's other arm. Similarly, it is not expected that persons having a natural infection of melioidosis, or horses or other animals having a natural infection of glanders, receiving a vaccine against a second pathogen, would develop an enhanced immune response to the second pathogen because of OMVs released naturally from the *Burkholderia* with which they are infected.

Without wishing to be bound by theory, it is believed that enhancement of a subject's immune response is due to antigen presenting cells, such as dendritic cells, encountering the adjuvant and the antigen together, which either does not happen or is significantly attenuated if the adjuvant and the antigen are administered at different sites. Accordingly, it is contemplated that, for use in injections, the BOMVs will be injected with the antigen or antigens of interest. In oral use, the BOMVs can be administered in the same liquid, powder or other form in which the antigen is being administered, or they can be, for example, administered immediately before or after the formulation containing the antigen or antigens. The compositions comprising the BOMVs may further contain pharmaceutically acceptable excipients suitable for maintaining desired properties for the intended route of administration, such as pH, salt content, anti-caking and other common characteristics familiar to those in the art of formulating vaccine compositions for use in various routes of administration.

As shown in the Examples, BOMVs were effective as adjuvants in in vivo models when administered orally, intranasally, or by injection. Accordingly, the immunogenic compositions of the invention can be administered by those routes, and are expected to be effective when administered by other conventional routes. The administration may be, for example, intravenous, intraperitoneal, intramuscular, intracavity, subcutaneous, intradermally or intranasally. In some particularly preferred embodiments, the administration is transdermal.

Definitions

As used herein, the term "immunogen" refers to a substance that has the ability to evoke an immune response, either by inducing generation of antibodies, by causing a cell-mediated immune response, or by inducing both an antibody and a cell-mediated immune response.

As used herein, the term "non-*Burkholderia* immunogen" refers to an immunogen which is not naturally present in members of the bacterial genus *Burkholderia*. In some embodiments, the "non-*Burkholderia* immunogen" is an immunogen expressed from a nucleic acid sequence introduced into a *Burkholderia* bacterium by genetic engineering In some embodiments, the non-*Burkholderia* immunogen is one expressed from a nucleic acid sequence introduced into a *Burkholderia* bacterium, which sequence encodes (a) a protein or peptide not naturally present in members of the bacterial genus *Burkholderia*, and (b) a *Burkholderia* protein or peptide which is normally present in the outer membrane vesicle of the *Burkholderia* bacterium into which the nucleic acid sequence has been introduced, wherein (a) and (b) are expressed as a fusion protein or peptide.

As used herein, "adjuvant" refers to a substance that is capable of enhancing, accelerating, or prolonging an immune response to an immunogen when co-administered with the immunogen.

"Outer membrane vesicles," which are sometimes referred to herein as "OMVs," are "spherical buds of the outer membrane filled with periplasmic content . . . commonly produced by Gram-negative bacteria." Schwechheimer and Kuehn, Nature Reviews Microbiology, 2015, 13:605-619 (see, abstract). Kaparakis-Liaskos and Ferrero state that OMVs are "spherical, bilayered membrane nanostructures that contain many components found within the parent bacterium." Kaparakis-Liaskos and Ferrero, Nature Reviews Immunology, 2015, 15:375-387 (see, abstract). See also, Kuehn and Kesty, Genes & Dev. 2005. 19: 2645-2655, Kulp and Kuehn, Annual Review of Microbiology, 2010, 64:163-184.

As used herein, "derived from," with respect to an immunogen, refers to obtaining an immunogenic component of a pathogen or a cancer cell by any of a number of means known in the art, such as by isolation of the immunogen from the native organism or by recombinant expression or synthesis Immunogens derived from a pathogenic organism may be treated before use to reduce undesired effects. For example, "toxoids" are bacterial toxins which have been treated to suppress or eliminate their ability to act as a toxin, while retaining their ability to induce an immune response against the bacteria from which the toxin originated. The term "derived from" also encompasses structures formed by proteins or peptides that have been recombinantly expressed, such as the virus-like particles that self-assemble from recombinantly expressed capsid proteins of viruses such as human papillomavirus.

As used herein, "co-administration" refers to co-localized administration of two or more agents, such as an immunogen and an adjuvant, to the same subject during a treatment period. The two or more agents may be encompassed in a single formulation and thus be administered simultaneously. Alternatively, the two or more agents may be in separate physical formulations and administered separately to the same spot in the subject, either sequentially or simultaneously. The term "administered simultaneously" or "simultaneous administration" means that the administration of the first agent and that of a second agent overlap in time with each other, while the term "administered sequentially" or "sequential administration" means that the administration of the first agent and that of a second agent does not overlap in time with each other, but takes place sufficiently close in time that the first agent has not been taken up or metabolized before administration of the second agent so that antigen-presenting cells "see" the first agent in conjunction with the second agent.

"Immune response" refers to any detectable response to a particular substance (such as an antigen or immunogen) by the immune system of a host vertebrate animal, including, but not limited to, innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids). Examples of immune responses include an alteration (e.g., increase) in Toll-like receptor activation, lymphokine (e.g., cytokine (e.g., Th1, Th2 or Th17 type cytokines) or chemokine) expression or secretion, macrophage activation, dendritic cell activation, T cell (e.g., CD4+ or CD8+T cell) activation, NK cell activation, B cell activation (e.g., antibody generation and/or secretion), binding of an immunogen (e.g., antigen (e.g., immunogenic polypolypeptide)) to an MHC molecule, induction of a cytotoxic T lymphocyte ("CTL") response, induction of a B cell response (e.g., antibody production), and, expansion (e.g., growth of a population of cells) of cells of the immune system (e.g., T cells and B cells), and increased processing and presentation of antigen by antigen presenting cells. The term "immune response" also encompasses any detectable response to a particular substance (such as an antigen or immunogen) by one or more components of the immune system of a vertebrate animal in vitro.

An "immunological response" to a selected antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes, by other white blood cells, or by both. One important aspect of cellular immunity involves an antigen-specific response by cytolytic T-cells ("CTLs"). CTLs have specificity for peptide antigens that are presented in association with proteins encoded by the major histocompatibility complex (MHCI) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHCII molecules on their surface. A "cellular immune response" also refers to the production of cytokines, chemokines and other such molecules produced by activated T-cells and/or other white blood cells, including those derived from CD4+ and CD8+ T-cells. A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art.

The terms "effective amount" or "pharmaceutically effective amount" of an adjuvant composition and antigen, as provided herein, refer to a nontoxic but sufficient amount of the composition to provide the desired response, such as an immunological response, and optionally, a corresponding therapeutic effect, or in the case of delivery of a therapeutic protein, an amount sufficient to effect treatment of the subject, as defined below. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

The phrase "pharmaceutically acceptable," in connection with administration of a substance to a human refers to a substance that is generally safe for human pharmaceutical use. In connection with administration to a non-human animal of a particular species, it refers to a substance that is generally safe and acceptable to a non-human animal of the species in question.

As used herein, the terms "pharmaceutically acceptable carrier" and "pharmaceutically acceptable vehicle" are interchangeable and refer to a fluid vehicle for containing vaccine immunogens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

Diseases for which BOMVs can be Used as Adjuvants

One hallmark of an effective adjuvant is that it increases the immune response of a subject to an immunogen. In preferred embodiments, the adjuvants are Bpc OMVs. In some embodiments, the Bpc OMV is from an attenuated member of the Bpc or one that is non-pathogenic to a subject to which it is to be administered. In veterinary uses, the subject is a non-human mammal, such as a horse, cow, sheep, pig, dog or cat. In some embodiments, the subject is a human. In some embodiments, the non-pathogenic *Burkholderia* for use with a human is *B. thailandensis*. In a particularly preferred embodiment, the Bpc OMVs are Bp82 OMVs.

In general, adjuvants increase the immune response to an immunogen and can be used with immunogens derived from a variety of pathogens. According to the website of the Centers for Disease Control and Prevention ("CDC"), for example, aluminum gels or salts (collectively, generally referred to as "alum") are used in vaccines against hepatitis A, hepatitis B, diphtheria-tetanus-pertussis (DTaP, Tdap), *Haemophilus influenzae* type b (Hib), human papillomavirus (HPV) and pneumococcus infection—that is, against infections caused by both viral and bacterial agents. As shown in the studies reported herein, the immune response raised by Bpc OMVs is broader than that of alum. It is therefore believed that Bpc OMVs can likewise be used as adjuvants to increase the immune response to at least the same types of pathogens as can alum, such as bacterial and viral antigens. For example, Bpc OMVs can be used to replace alum as an adjuvant in each of the vaccines noted above, or can be used in addition to alum, to provide an enhanced immune response to already existing vaccines.

The studies reported in the Examples demonstrate that an exemplar Bpc OMV surprisingly enhanced the immune response of mice to DAPTACEL®, a current, commercially-available vaccine. The vaccine contains two types of antigens: toxoids from the bacteria *Corynebacterium diphtheriae*, and *Clostridium tetani*, and killed whole cells of *Bordetella pertussis*. Further, the three bacteria to which the vaccine provides protection are not only from three different genuses, but also three different taxonomic orders, two are Gram positive, while one is Gram negative, and two are aerobes, while one is an obligate anerobe. The studies reported below further show that mice vaccinated with heat-killed *Salmonella typhimurium* (a Gram negative facultative anaerobe) in combination with the exemplar Bpc OMVs were protected when subsequently challenged with live, wild-type *S. typhimurium.*

The fact that the exemplar Bp OMVs maintained or potentiated the response to four different types of bacteria (the three bacteria targeted by DAPTACEL®, plus heat-killed *Salmonella*) indicates that Bpc OMVs can be used as adjuvants to potentiate vaccines against both Gram negative and Gram positive bacteria, against aerobes, facultative anaerobes, and aerobes, and in vaccines using toxoids, heat-killed bacteria, or both. Thus, it is expected that Bpc OMVs can be used as adjuvants to potentiate vaccines against a wide range of bacteria, including, but not limited to, *Bacillus, Rickettsia, Chlamydia, Chlamydophila, Mycobacteria, Salmonella*, Spirochete (including *Borrelia burgdorferi, Borrelia recurrentis, Treponema pallidum*, and Leptospira), *Shigella, Listeria*, and *Mycoplasma.* Vaccines for many of these bacteria which can be potentiated by Bpc OMVs are known or under development, as exemplified by vaccines against Lyme disease (see, e.g., U.S. Pat. Nos. 9,562,080; 9,534,021; 8,821,893; and 8,414,901); anthrax (see, e.g., U.S. Pat. Nos. 9,816,117 and 8,778,359), pneumococcal polysaccharides vaccine, *haemophilus* b conjugate (PRP-T) vaccine, meningococcal conjugate vaccine, meningococcal groups A, C, Y, and W-135 vaccine, typhoid vaccine (inactivated), and cholera vaccine. See also, Detmer and Glenting, Microb Cell Fact. 2006; 5: 23. The immunogen in the vaccine may be, for example, a killed or an inactivated bacterium, such as is used in vaccines against cholera, plague, typhus, and Q fever, a live attenuated bacterium, such as in BCG vaccine, a capsular polysaccharide, alone or conjugated to a carrier protein, such as are used in vaccines directed against *Streptococcus pneumoniae, Haemophilus influenzae, Neisseria meningitidis*, and *Salmonella typhi*, a toxoid, as discussed above with regard to diphtheria and tetanus, or a purified or recombinant protein, such as is used in the acellular pertussis vaccine.

According to the Institute for Vaccine Safety (Johns Hopkins Bloomberg School of Public Health), DAPTACEL®, is adjuvanted with 0.33 mg aluminum phosphate. Since immunogenic compositions with Bpc OMVs are or are expected to be superior to alum adjuvants in inducing cellular immunity, and as intracellular infectious pathogens and cancer are eliminated from the body by cellular immunity, the inventive immunogenic compositions are also expected to be superior agents for raising immune responses to pathogens, including intracellular infectious pathogens, such as *Mycoplasma*, that are particularly hard to target with vaccines adjuvanted with currently available adjuvants. Mycomplasma vaccines that can be potentiated by being adjuvanted with Bpc OMVs include, for example, those taught in U.S. Pat. Nos. 9,982,039, 9,730,992, and 9,636,391.

Similarly, the inventive immunogenic compositions are expected to be superior adjuvants for raising immune responses to viruses, such as rabies virus, herpesviruses, such as herpes simplex virus (HSV) type 2, HSV type 1, human cytomegalovirus, Epstein-Barr virus, and varicella zoster virus (VZV), human papillomavirus (HPV), Human T-cell lymphotropic virus type 1, rotavirus, norovirus, hepatitis A virus, hepatitis B virus, hepatitis C virus, influenza virus, polio virus, Japanese encephalitis virus, measles virus, mumps virus, rubella virus, yellow fever virus, varicella virus, dengue virus, rotavirus, parvovirus, human immunodeficiency virus-1, ebolaviruses, such as Ebola Sudan virus, Marburg virus, hantavirus, norovirus, Zika virus, West Nile virus, hantavirus, Lassa virus, Lymphocytic choriomeningitis virus, Nipah virus, Rift Valley fever virus, Middle East Respiratory Syndrome Coronavirus, SARS coronavirus, Crimean-Congo hemorrhagic fever virus, enteroviruses, and noroviruses.

Vaccines for many of these viruses, such as poliovirus, mumps virus, papillomavirus, and dengue, are commercially available. All commercially available vaccines that are adjuvanted are adjuvanted with adjuvants other than Bpc OMVs. It is contemplated that the immune response to currently approved vaccines against viruses can be improved by use of Bpc OMVs as an adjuvant in place of, or in addition to, the adjuvant or adjuvants currently used in the vaccines. Other viruses, such as HIV-1, ebola, and Zika virus, have vaccines in development that provide some protection against infection or against severe infection. It is anticipated that adjuvanting vaccines for such viruses with Bpc complex OMVs will augment the protection provided by the current vaccine candidates. It is noted that, with viruses such as HIV-1 and ebola, a vaccine that provides even partial protection can itself constitute an important public health advance.

Vaccines in production or development against viruses that can be potentiated by adjuvanting with Bpc OMVs include vaccines against West Nile Virus (see, e.g., U.S. Pat. No. 9,962,435), enteroviruses (see, e.g., U.S. Pat. No. 9,987,350), noroviruses (see, e.g., U.S. Pat. No. 9,867,876), herpes simplex 2 (see, e.g., U.S. Pat. Nos. 9,919,045; 9,895,436. 9,566,325, and 9,555,100), cytomegalovirus (see, e.g., U.S. Pat. No. 9,901,632), dengue fever (see, e.g., U.S. Pat. Nos. 9,861,692, 9,783,787, 9,463,235, RE 46,641, and RE 46,631), and chikungunya virus (see, e.g., U.S. Pat. No. 9,844,588).

Bpc OMVs can also be used to potentiate the immune response to viral antigens other than those targeted by current vaccines. In this regard, it is noted that the complete genomes for all or most of these viruses are known, as are the coding sequences of the various proteins of these viruses, which can be used to raise immune responses against the viruses. For example, the complete genome sequences of numerous isolates of Ebola virus have been deposited in GenBank, as exemplified by Ebola virus isolate Ebola virus/*H. sapiens*-tc/COD/1995/Kikwit-9510622 under accession number KU182909. Similarly, the complete genome of isolates of Marburg virus are available on GenBank, as exemplified by the genome of Marburg virus isolate Marburg virus/RML-IRF/M.auratus-lab/AGO/2005/Angola-368-HA, available under accession number KY047764. The complete genome of Nipah virus is available in GenBank under accession number NC_002728. The complete genome of West Nile virus used by the CDC as a reference reagent is available in GenBank under accession number AY646354 (see, e.g., Grinev et al., Genome Announc 2 (5) (2014). The complete genome of isolates of Zika virus are available in GenBank, as exemplified by the sequence for Zika strain Zika virus/*Homo sapiens*/VEN/UF-2/2016, available under accession number KX893855 (see, e.g., Blohm et al., Genome Announc 5 (17), e00231-17 (2017)). The complete genome of yellow fever virus is available in GenBank under accession number NC_002031 (see, e.g., Rice, et al., Science 229 (4715), 726-733 (1985)). The complete genome of isolates of Middle East respiratory syndrome coronavirus are available on GenBank, as exemplified by the genome of isolate Camel/UAE/D1243.12/2014 deposited under accession number KP719932.

Persons of skill can use proteins, virus-like particles formed by viral capsid proteins, or other immunogens encoded by the genome, including proteins or immunogens already in trials as vaccine candidates or in currently approved vaccines, and use them as immunogens in the inventive compositions and methods to enhance a subject's immune response to the immunogen compared to the same immunogen adjuvanted with a conventional adjuvant.

In some embodiments, the present invention will find use for enhancing an immune response against proteins or other immunogens from the various human herpesviruses. Such herpesviruses include, for herpes simplex viruses (HSV)-1 and -2 and proteins derived from such HSVs, such as HSV-1 and HSV-2 glycoproteins gB, gD and gH. The complete genomes of various strains of HSV-1 have been sequenced and deposited in GenBank. See, e.g., accession number X14112, version X14112.1, accession number MH999839 (strain K86), accession number MH999841 (strain Ty148). The complete genomes of various strains and isolated of HSV-2 have also been sequenced and deposited in GenBank. See, e.g., accession number KY922726 (complete genome of isolate HSV2-H12212); and accession number NC_001798, version NC_001798.2 (strain HG52).

The complete genomes for a number of strains of human herpesvirus 3, or Varicella zoster virus (VZV) are also set forth in GenBank. See, e.g., accession number NC_001348 (Davison and Scott, J. Gen. Virol. (1986) 67:1759-1816), accession number DQ674250, for strain NH29_3, and accession number DQ479963, for strain 32, passage 72 (see, Peters et al., J. Virol. 80 (19), 9850-9860 (2006)). Similarly, the complete genomes of various strains of human cytomegalovirus (CMV) have been sequenced and deposited in GenBank (see, e.g., accession number X17403 (strain AD169, Chee et al., Curr. Top. Microbiol. Immunol. 154, 125-169 (1990) and Bankier et al., DNA Seq. 2 (1), 1-12 (1991)), and accession number NC_006273 (strain Merlin, Gatherer et al., Proc. Natl. Acad. Sci. U.S.A. 108 (49), 19755-19760 (2011)).

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the compositions and methods described herein. With respect to hepatitis A, the complete genome of the wild-type virus was deposited in GenBank in 1987 under accession number M14707 (see, Cohen et al., J. Virol. 61 (1), 50-59 (1987)), and the genomes of various isolates have also been deposited. See, e.g., accession number KP879216 for isolate 18f (see, Lemon et al., J. Virol. 65 (4), 2056-2065 (1991), and accession number AB279734, for isolate HAJ95-8 (see, Endo et al., Virus Res. 126 (1-2), 116-127 (2007). With respect to hepatitis B, the entire genome of various strains and isolates are set in GenBank, as exemplified by accession numbers AF363962 (strain G683-2) and AB775201 (isolate HB12-0929). The genome of various isolates and strains of HCV are likewise deposited in GenBank. For example, the sequence of the entire genome of HCV genotype 1 is available under accession number NC-004102, which also sets forth annotations of the mature proteins from the literature. Further, the complete sequence for HCV subtype 6a, strain 6a74, can be found in GenBank under accession number DQ480524, while that of HCV subtype 6A, strain 6a67 can be found under accession number DQ480520.

Antigens derived from other viruses can also be used in embodiments of the inventive compositions and methods, such as, without limitation, proteins from members of the families Picornaviridae (e.g., polioviruses, etc.); Caliciviridae; Togaviridae (e.g., rubella virus, dengue virus, chikungunya virus, etc.); Flaviviridae; Coronaviridae; Reoviridae; Birnaviridae; Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; and Retroviradae (e.g., HIV-1 (the complete genome of HIV-1 is set forth in GenBank under accession number NC_001802, along with the sequences of numerous proviral genomes and genomes of isolates) and HIV-2 (the complete genome of HIV-2 is set forth in GenBank under accession number NC_001722, along with numerous proviral genomes and the genomes of numerous isolates and clones); simian immunodeficiency virus (SIV), feline immunodeficiency virus (FIV), human papillomavirus (HPV), and the tick-borne encephalitis viruses. See, e.g. Burrell et al., Eds., Fenner and White's Medical Virology, 5$^{th}$ Ed. (Academic Press, London, 2017); Collier et al., Human Virology, 4$^{th}$ Ed. (Oxford Univ. Press, Oxford, U K, 2017), and Murray et al., Medical Microbiology, 8$^{th}$ Ed. (Elsevier, Philadelphia, PA, 2016), each of which is incorporated herein in its entirety, for a description of these and other viral pathogens. The complete genomes of most or all of these viruses, including the various types of papilloma virus associated with warts or cervical cancer, have been sequenced and deposited in GenBank, as exemplified by the complete genome for HPV 16, deposited under accession number NC_001526.

As noted above, influenza virus is an example of a virus for which the present invention is expected to be useful. Specifically, the envelope glycoproteins HA and NA of influenza A are of particular interest for generating an immune response. Numerous HA subtypes of influenza A have been identified and sequenced, as exemplified by the sequence of HA segment 4 deposited in GenBank under accession numbers NC-026433 and FJ966974 (see, Garten et al., Science 325 (5937), 197-201 (2009). Proteins or other immunogens derived from any of these isolates can also be used in the invention described herein.

Further, since adjuvants provide a general increase in immune response to antigens with which they are presented in combination, it is believed that Bpc OMVs will also increase a subject's immune response to parasites and can be used as adjuvants in human and veterinary vaccines currently in use or under development against parasitic diseases including, but not limited to, malaria (see, e.g., U.S. Pat. Nos. 9,943,580; 9,616,115; 9,603,916; and 9,592,282. See also, Coelho et al., Advances in malaria vaccine development: report from the 2017 malaria vaccine symposium, npj Vaccines 2, Article number: 34 (2017), doi: 10.1038/s41541-017-0035-3) or to increase the immune response to the RTS,S/AS01 vaccine currently in trials with a liposome-based adjuvant (see, e.g., Gosling R, von Seidlein L (2016)). Vaccines against other parasitic diseases that can potentiated by use of Bpc OMVs include diseases caused by helminths, such as schistosomiasis (reviewed in Tebeje, et al., Schistosomiasis vaccines: where do we stand? Parasites & Vectors, 2016, 9:528, see also, e.g., U.S. Pat. No. 9,248,169) and hookworm (see, e.g., U.S. Pat. No. 8,444,994), as well as diseases caused by other parasites, such as leishmaniasis (see, e.g., Gillespie, et al., Status of vaccine research and development of vaccines for leishmaniasis, 2016, Vaccine, 34(26): 2992-2995 and U.S. Pat. Nos. 9,764,015; 8,986,711; and 8,968,749), toxoplasma (see, e.g., Liu et al., Hum Vaccin Immunother. 2012 Sep. 1; 8(9): 1305-1308, and U.S. Pat. No. 9,802,974), and diseases caused by trypanosomes (see, e.g., Cazorla et al., Expert Rev of Vaccines, 2009, 8(7):921-931, doi.org/10.1586/erv.09.45 and LaGreca and Magez, Human Vaccines, 2011, 7(11):1225-33, doi.org/10.4161/hv.7.11.18203).

Further, it is believed that Bpc OMVs will also increase a subject's immune response to immunogens from invasive fungi, and can thus be used as adjuvants in vaccines against fungal infections (reviewed in, e.g., Spellberg, Vaccines for invasive fungal infections, F1000 Med Rep. 2011; 3: 13, doi: 10.3410/M3-13; Cassone and Casadevall, Recent Progress in Vaccines against Fungal Diseases, Curr Opin Microbiol. 2012 August; 15(4): 427-433). Vaccines comprising immunogens raising an immune response to pathogenic fungi are taught in, for example, U.S. Pat. Nos. 9,914,917; 9,364,539; and 8,449,894, and U.S Patent Pub. 2014/271720. Vaccines in which Bpc OMVs can be used as an adjuvant include vaccines against fungal pathogens, particularly those within one of the following genera: *Aspergillus, Pneumocystis, Histoplasma, Coccidioides, Malassezia, Blastomyces*, or *Candida*.

Bpc OMVs can also be used to generate immune responses to antigens expressed by cancer cells that are either not expressed on normal tissues, or that are found on tumors of a tissue type that is not of an essential human tissue (e.g., prostate antigens). Bpc OMVs can be used to enhance humoral and cell-mediated immune responses against antigens expressed by these cancer cells. Such antigens include activated oncogenes, fetal antigens, and activation markers. A number of tumor antigens have been explored for use as cancer vaccines, including the various MAGEs (melanoma associated antigen E), including MAGE 1, 2, 3, 4, etc. (reviewed in Xiao and Chen, World J Gastroenterol. 2004 Jul. 1; 10(13): 1849-1853), MART 1 (melanoma antigen recognized by T cells), mutant K-ras (see, e.g., Weden et al., Int J Cancer, 2011 Mar. 1, 128(5): 1120-1128 (https://doi.org/10.1002/ijc.25449), mutant p53, and carcinoembryonic antigen (CEA). A number of universities and companies are now developing cancer vaccines against tumor-associated antigens, as exemplified by U.S. Pat. Nos. 9,932,384; and 9,908,922, growth factors or variants of growth factors that are overexpressed in some cancer types, such as EGFR (see, e.g, U.S. Pat. No. 9,808,516), or modified heat shock proteins (see, e.g, U.S. Pat. No. 9,238,064), or neoantigens derived from the tumors of individual patients. Some cancer vaccines are intended to raise an immune response to body tissues found on metastatic disease but not normal body tissues. It is expected that any of these cancer vaccines can be potentiated by being adjuvanted with Bpc OMVs.

Further, companies are currently engineering T-cells with chimeric antigen receptors ("CARs") as part of what is known as CAR T-cell therapy, and introducing the engineered T-cells into subjects so the engineered cells can recognize and kill tumor cells bearing antigens recognized by the CAR. It is believed that Bpc OMVs can be used as an adjuvant to potentiate immune responses against cancer antigens, such as those targeted by CAR-T therapy. As a number of tumor antigens have been and are being explored for in CAR-T therapy, it is expected that the person of skill is familiar with the selection of appropriate tumor antigens for use in embodiments of the inventive compositions and methods.

In some embodiments, the Bpc OMVs are useful to potentiate vaccines against opioid drugs, such as fentanyl, heroin, and oxycodone. These vaccines are typically designed to raise antibodies intended to intercept the opioid in the user's bloodstream before the opioid reaches the user's brain and induces an enjoyable response. One problem in the development of opioid vaccines to date has been with the limited effectiveness with which the vaccines induce an antibody response. It is expected that Bpc OMVs, with their ability to induce a robust antibody response, will increase the effectiveness of such vaccines. The vaccine or vaccines can be administered, for example, to those with a past problem with addiction to one or more opioids, thereby reducing their risk of readdiction, or to those currently addicted to an opioid drug to reduce pleasant effects from their use of the drug.

Fentanyl and some of the other opioids are relatively small molecules and their immunogenicity may be improved by use of a hapten. Methods of conjugating molecules to various opioids are known. For example, oxycodone has been conjugated to various haptens, such as keyhole limpet hemocyanin subunit dimer. (See, e.g., Barrufaldi et al., Mol Pharm. 2018 Nov. 5; 15(11):4947-4962. doi: 10.1021/acs.molpharmaceut.8b00592. Epub 2018 Oct. 10, and Raleigh et al., PLoS One. 2017 Dec. 1; 12(12):e0184876. doi: 10.1371/journal.pone.0184876. eCollection 2017). Hwang et al. have reported on the development of a vaccine containing an admixture of heroin and fentanyl-hapten conjugates. See, Hwang et al., ACS Chem Neurosci. 2018 Jun. 20; 9(6):1269-1275. doi: 10.1021/acschemneuro.8b00079. Epub 2018 Mar. 23. See also, Raleigh et al., J Pharmacol Exp Ther. 2019 February; 368(2):282-291. doi: 10.1124/jpet.118.253674. Epub 2018 Nov. 8, Hwang and Janda, Biochemistry. 2017 Oct. 24; 56(42):5625-5627. doi: 10.1021/acs.biochem.7b00948. Epub 2017 Oct. 10, and Olson and Janda, EMBO Rep. 2018 January; 19(1):5-9. doi: 10.15252/embr.201745322. Epub 2017 Dec. 13.) It is anticipated that Bpc OMVs can be added to these and similar vaccine formulations to potentiate their immunogenic effects. In some embodiments, the fentanyl or other opioid to be targeted may be chemically conjugated to the Bpc OMVs by conventional chemistry, such as that used to create the fentanyl-hapten conjugates used in the studies reported above, to act both as a hapten and as an adjuvant to potentiate the immunogenic effect of the opioid moiety.

Any particular immunogen of interest can be readily tested to determine if administering it in combination with Bpc OMVs raises a better immune response than the immunogen alone, or a combination of the immunogen and a standard adjuvant, such as alum, by testing the combination of choice in standard assays, such as the assays set forth in the Examples, below.

*Burkholderia*, B. *Pseudomallei* Complex, and Bpc OMVs

According to Wikipedia, "*Burkholderia*" refers to "a group of virtually ubiquitous Gram-negative, obligately aerobic, rod-shaped bacteria that are motile by means of single or multiple polar flagella, with the exception of *Burkholderia mallei* which is nonmotile." Baker 2017, supra, reports that *B. mallei* evolved from *B. pseudomallei* through genome reduction and that many virulence determinants including surface polysaccharides, outer membrane proteins, secretion systems, and motility proteins, are highly conserved between the two species. Accordingly, the OMVs of *B. mallei* should have the same effectiveness as adjuvants as those of *B. pseudomallei. B. thailandensis* is considered to be very close to *B. pseudomallei*, but rarely causes pathology in humans.

Price et al. "Improved multilocus sequence typing of *Burkholderia pseudomallei* and closely related species," Journal of Medical Microbiology (2016), 65, 992-997, doi: 0.1099/jmm.0.000312, ("Price 2016," the entirety of which is incorporated herein by reference) proposes an expanded *B. pseudomallei* complex ("Bpc") based on the phylogenetic relatedness of *B. pseudomallei* and its nearest neighbors. According to Price 2016, the Bpc comprises *B. pseudomallei, B. mallei, B. oklahomensis, B. thailandensis, B. humptydooensis* (proposed), and three unassigned *Burkholderia* spp. Clades A (represented by type strain BDU 5), B (represented by type strain BDU 8) and C (represented by type strain MSMB0265). The same expanded membership of the classical Bpc is also set forth in Lowe et al., PLoS ONE 11(10): e0164006. Doi.org/10.1371/journal-.pone.0164006 ("Lowe 2016," the entirety of which is incorporated herein by reference), which states that the three clades have not been assigned a species but are *B. thailandensis*-like strains most related to *B. oklahomensis. B. humptydooensis* is further described in Tuanyok, et al., "*Burkholderia* humptydooensis sp. nov., a new species related to *Burkholderia thailandensis* and the fifth member of the *Burkholderia pseudomallei* complex," 2017, Appl Environ Microbiol 83:e02802-16. Doi.org/10.1128/AEM.02802-16. See also, Gee J E, et al., "Recovery of a *Burkholderia thailandensis*-like isolate from an Australian water source," BMC microbiology. 2008; 8:54. Epub 2008/04/04. pmid: 18384685; Glass M B, et al., "*Burkholderia oklahomensis* sp. nov., a *Burkholderia pseudomallei*-like species formerly known as the Oklahoma strain of *Pseudomonas pseudomallei*," International J Systematic Evolut Microbiol, 2006; 56(9):2171-6. Epub 2006/09/08. pmid:16957116; Ginther, et al., "Identification of *Burkholderia pseudomallei* Near-Neighbor Species in the Northern Territory of Australia," PLoS neglected tropical diseases, 2015; 9(6):e0003892. Epub 2015/06/30. pmid:26121041.

The American Type Culture Collection ("ATCC") website showed, as of April 2018, the availability of over 20 species of *Burkholderia* and a number of strains or isolates of particular species, other than *B. pseudomallei* or *B. mallei*. Strains of *B. pseudomallei* and of *B. mallei* are available to persons registering with the Biodefence Emerging Infections Research Resources Repository ("BEI"), run by the ATCC under contract from the National Institute of Allergy and Infectious Diseases (registration requires, among other things, demonstrating that the requestor has facilities suitable for the biosafety level of the organisms requested). A review of the BEI's website indicates that, as of April 2018, it had available over 40 strains of *B. pseudomallei*, over 10 strains of *B. mallei*, and 5 strains of *B. thailandensis*. Bp strain 1026b is available from BEI under accession number NR-4074. Probst et al., Infection and Immunity, 2010,78(7): 3136-3143, describes how to make a ΔpurM mutant of Bp strain 1026b, resulting in a mutant form of Bp 1026b they term "Bp82". Torres, U.S. Patent Application Publication 2017/0333543 also describes producing *Burkholderia*, and particularly *B. mallei*, whose pathogenicity is attenuated by deletion or disruption of the tonB and hcp1 genes. *Burkholderia* whose pathogenicity is attenuated as taught in Torres may be used to produce BOMVs for use in embodiments of the inventive compositions and methods.

The BEI website further states that the complete genome of *B. pseudomallei* strain 1106c is available under accession numbers CP000572.1 and CP000573.1, for chromosomes 1 and 2, respectively. The website states the genome of *B. thailandensis* strain E264 has been sequenced and is available under assembly no. ASM1236V.I. *B. humptydooensis* is available from the ATCC® under accession number BAA2767™. *B. oklahomensis* is available from the Leibniz Institute DSMZ-German Collection of Microorganisms and Cell Culture, Braunschweig, Germany.

Figure 1:
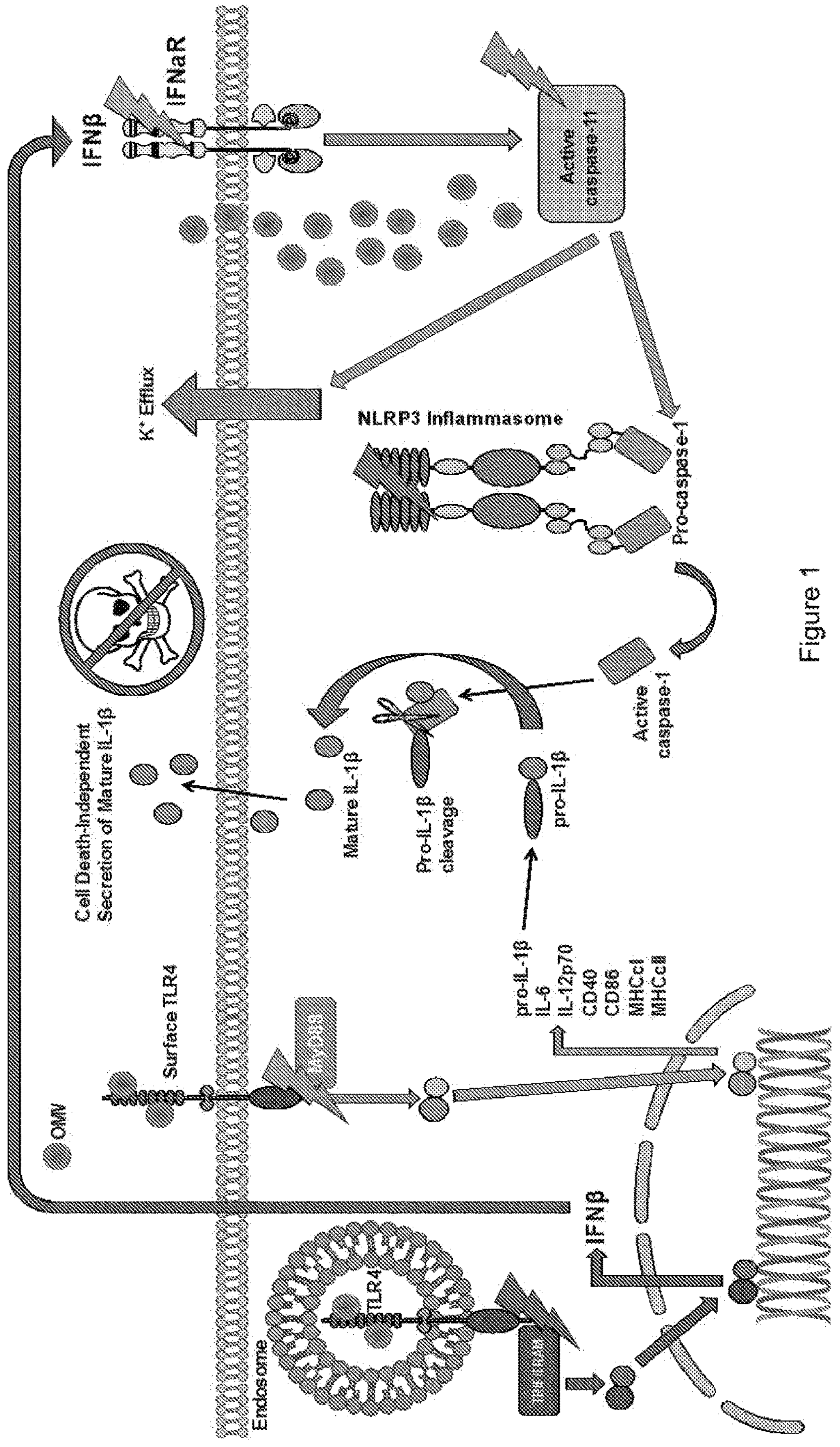
FIG. 1 is a cartoon showing the engagement of outer membrane vesicles with extra- and intra-cellular pathogen recognition and signaling pathways. OMV=outer membrane vesicles.

FIG. 1 is a cartoon showing that OMVs engage both extra- and intra-cellular pathogen recognition and signaling pathways. OMVs signal through surface and endosomal TLR4 following phagocytosis, leading to the upregulation of dendritic cell activation markers, T cell polarizing cytokines, pro-IL-1β, and type 1 IFNs. OMVs also enter the cytosol through membrane fusion and mediate the activation of caspase-11 directly and indirectly through type 1 IFN signaling. Caspase-11 activation leads to K+ Efflux, subsequent NLRP3 activation and the secretion of caspase-1-dependent mature IL-1β secretion in the absence of cell death.

OMVs have lumens and the lumens contain bacterial components. In some embodiments, the member of the Bpc from which the OMVs are obtained can be genetically engineered by conventional techniques to overexpress the immunogen of choice so that it present in the organism's cytoplasm, periplasm or membrane. In these embodiments, the lumen of the OMVs encapsulates one or more of these fractions containing the immunogen. Once administered to a subject, the encapsulated immunogen is protected from proteases present in the subject until the OMV is taken up by a phagocyte and degraded. Without wishing to be bound by theory, it is contemplated that the phagocytes taking up such OMVs will present the combination of the immunogen and the OMVs to the subject's T cells, resulting in raising an immune response to the immunogen stronger than that raised by administration of the immunogen alone. OMVs encapsulating an immunogen can be administered by themselves or, in some embodiments, are co-administered with additional immunogen to raise an even greater immune response to the immunogen.

In some embodiments, the member of the Bpc from which the OMVs are obtained can be genetically engineered by conventional techniques (such as by adding an appropriate leader sequence) to express the immunogen of choice so that it is expressed on the surface of the bacterial cell and incorporated into the surface of the OMVs as they are released from the cell. In some embodiments, the bacterial cell may be engineered with a nucleic acid sequence encoding the immunogen in line with a protein known to be found on the surface of the OMVs, so that the immunogen is expressed as a fusion protein with the protein and is present on the surface of the bacterium's OMVs. Without wishing to be bound by theory, it is contemplated that, when administered to a subject, OMVs will present the immunogen to the subject's B cells, resulting in the subject raising an immune response to the immunogen that is stronger than that which would be raised by the immunogen was administered to the subject by itself. OMVs bearing an immunogen in their lumen or on their surface can be administered as a vaccine by themselves or, in some embodiments, may be co-administered with additional immunogen to raise an even greater immune response to the immunogen.

Formulations, Dosage, and Administration

Formulation and administration of vaccines, and the use of adjuvants is well known, as exemplified by U.S. Pat. Nos. 6,869,607 and 7,371,395. The immunogens used in vaccines traditionally have included killed or attenuated pathogens, such as viruses, bacteria, or protozoans. In some embodiments, a vaccine containing killed or attenuated pathogens may be adjuvanted with Bpc OMVs to enhance its immunogenicity. More recent vaccines contain synthetic or recombinant proteins or peptides or, in the case of some viruses, empty virus-like particles formed of viral capsid proteins. See, e.g., U.S. Pat. Nos. 7,192,595; 6,194,546; 5,962,298; 5,716,620, and 5,437,951. See also, e.g., Schijns and O'Hagan, Immunopotentiators in Modern Vaccines, 2nd Ed., (Academic Press, London, 2017). Recombinant proteins or peptide vaccines are considered as safer than vaccines containing killed or attenuated pathogens, but are often less immunogenic. In some embodiments, such vaccines and other vaccines with less immunogenicity than may be desired may be adjuvanted with Bpc OMVs to enhance their immunogenicity.

In some embodiments, the inventive vaccine compositions comprise an immunologically effective amount of the desired immunogen and an immunologically effective amount of Bpc OMV as an adjuvant. Stabilizers, buffers, and other agents known in the art may be added to the vaccine formulation, based on considerations such as how the vaccine composition is going to be stored and the intended route of administration. It is expected that persons of skill in the art are familiar with determining whether any particular vaccine formulation should contain a stabilizer, a buffer, excipients, or other reagents to maximize the shelf-life, effectiveness, or other characteristics of the vaccine. While characteristics of a vaccine formulation may be enhanced by the presence of stabilizers, buffers, or other reagents, the improved immune response to a vaccine formulation comprising a desired immunogen and Bpc OMVs as an adjuvant compared to the same immunogen adjuvanted with another adjuvant is understood to due to the response by the subject's immune system to the immunogen when the immunogen is presented to the subject's immune system in combination with Bpc OMVs.

By "immunologically effective amount", it is meant that the administration of that amount to an individual, either in a single dose or as part of a series, is effective in raising an immune response that can ameliorate the symptoms of a disease or condition, or prevent the patient from developing the disease or condition. This amount typically varies depending upon the health and physical condition of the individual to be treated, age, the taxonomic group of individual to be treated (e.g. primate, equine, bovine, porcine, feline, canine, camelid, etc.), the capacity of the individual's immune system to synthesize antibodies or to initiate a cell-mediated immune response, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The vaccine composition may be administered in conjunction with other immunoregulatory agents. Both human and veterinary uses of the inventive compositions and methods are contemplated.

The immunogenic compositions of some embodiments of the invention are preferably administered in effective amounts. An "effective amount" is that amount of a vaccine or immunogenic composition that alone or together with further doses, produces the desired response. In the case of preventing or reducing the severity of a selected infectious disease, the desired response is providing some or complete protection from infection, or amelioration of symptoms, in an individual challenged by an agent that causes the selected infectious disease, compared to an individual who has need received the immunogenic composition. In the case of treating a particular cancer, the desired response is providing an immune response that causes a slowing of the growth of, or a regression in size of, one or more tumors, or, for blood cancers, a reduction in the number of cells of the blood cancer per mL of the patient's blood. In the case of compositions intended to affect a patient's response to an opioid or other addictive agent, the desired response is in blocking or reducing the effect of the addictive agent in the patient.

As persons of skill in the art are aware, the amounts of immunogens and of adjuvants needed to induce an immune response to a typical vaccine are quite small. For example, the Institute for Vaccine Safety states that the DAPTACEL® vaccine contains 10 mcg of pertussis antigen, and 0.33 mg of aluminum phosphate as adjuvant, while the competing INFANRIX® vaccine contains 25 mcg of pertussis antigen and 0.625 mg of aluminum hydroxide as adjuvant. The Institute further reports that a 0.5 mL dose of the anti-HPV vaccine GARDASIL® contains the following amounts of antigens: 20 mcg of HPV 6 L1 protein, 40 mcg of HPV 11 L1 protein, 40 mcg of HPV 16 L1 protein, 20 mcg of HPV 18 L1 protein, and 225 mcg of amorphous aluminum hydroxyphosphate sulfate adjuvant.

Typically, immunogenic compositions are prepared as injectables, either as liquid solutions or suspensions; solid forms suitable for solution in, or suspension in, liquid vehicles prior to injection may also be prepared. The preparation also may be emulsified for enhanced effect. It is contemplated that compositions comprising an immunogen and Bpc OMVs may be lyophilized to improve their shelf-life and to reduce or remove the necessity for cold storage. Such lyophilized compositions are typically mixed with a suitable liquid carrier, such as sterile saline, prior to administration to the subject.

Direct delivery of the compositions will generally be parenteral (e.g. by injection, either subcutaneously, intraperitoneally, intravenously or intramuscularly or delivered to the interstitial space of a tissue). Other modes of administration include oral and pulmonary administration, suppositories, and transdermal or transcutaneous applications, needles, and sprays. Cancer vaccines for solid tumors may further be injected directly into a tumor, into tissue immediately adjacent to a tumor, or both. As noted above, administration may be on a single dose schedule or a multiple dose schedule (e.g. including booster doses).

EXAMPLES

Example 1

This Example discusses routes by which Bpc OMVs can act as adjuvants.

The inventive compositions can provide protective immunity against a multitude of pathogenic organisms. It is known that protection against different types of pathogens relies on differing types of immunity (i.e. ideal protection against *Salmonella* infection requires Th1 helper T cells). *Salmonella* organisms enter the host using different mucosal access points; however, based on our data, use of Bpc OMVs induce wide-ranging immune responses that are capable of blocking and clearing pathogenic organisms entering at these sites. Notably, Bpc OMVs appear capable of driving immune responses that are far more diverse than any other adjuvant presently available in the current stable of vaccines. For example, alum (the adjuvant of choice for the clear majority of currently licensed vaccines) drives a predominantly Th2 helper T cell response, which can excel at combatting certain extracellular pathogens but is less capable of clearing other types of organisms, particularly intracellular pathogens.

Despite the prevalent use of alum as an adjuvant, its mechanism of activity remains somewhat elusive. Other approved adjuvants, such as monophosphorylipid A (MPL), act on toll like receptor 4 (TLR) via the MyD88 pathway to induce an immune response. This mechanism of action leads predominantly to a Th1 T cell response which is most efficient at clearing intracellular bacterial pathogens but less efficient at combatting extracellular pathogens and viruses. An adjuvant possessing unique mechanisms of adjuvanticity would circumvent the issues of singular immune responses (Th1 or Th2 or Th17) and instead could drive multifunctional immunity (Th1 and Th2 and Th17). Our data shows that Bp OMVs have this potential by engaging unique adjuvant pathways.

Unlike MPL, Bp OMVs (and, by extension, Bpc OMVs) can target not only TLR4, but also act through the inflammasome pathway, targeting Caspase-11 directly intracellularly in the absence of cell death. This is achieved through fusion of the Bpc OMVs with the cell membrane and subsequent entry or leakage into the cytosol. This distinctive combination of mechanistic targets leads to the diversity of the immune response observed with Bpc OMV immunization. Recent discussions in the scientific literature have raised the concept of "rational adjuvant design," highlighting the need to develop adjuvants that involve multiple arms of the immune system by targeting certain cellular responses; however, with the Bpc OMV adjuvant, nature has already solved this problem, allowing us to drive vaccine responses that are more diverse than other adjuvants and to target intracellular and extracellular bacterial and viral pathogens.

Example 2

This Example shows that Bpc OMVs can be produced with high stability.

An essential aspect of any vaccine formulation is the ability to develop consistent product, including adjuvant, from lot to lot. The outcome of such production requires that the immune response to the adjuvant also maintain consistency such that protection against infection is preserved. Bpc OMVs are produced through a biological process and as such, we have carefully measured lot to lot consistency of the Bpc OMV product over time to assure that each batch is reliably stable. This demonstrates that Bpc OMVs can be consistently and reliably produced to the same standards over time.

While lot-to-lot consistency is essential to adjuvant production, two other aspects of manufacture must also be considered pertaining to creation of Bpc OMVs. The first of these is the stability and long-term storage capacity of the adjuvant. Most beneficial would be a product that could be stored without being subject to cold chain (allowing for potential transport and use in warm climates). Bpc OMVs can be lyophilized and reconstituted or stored for over a month at 37° C. with no effect on immunological activity. This demonstrates that Bpc OMVs are ideal to include in vaccine preparations where a cold chain is unavailable, making Bpc OMVs an excellent adjuvant for vaccines for use in developing countries.

Example 3

This Example shows that testing of exemplar Bpc OMVs in multiple in vitro and in vivo model systems demonstrated their safety for use as adjuvants.

Any adjuvant intended for veterinary or human use must be safe for the intended use. We have evaluated safety in several models and have found the exemplar Bpc OMVs to be exceptionally well-tolerated. Indeed, Bpc OMVs are safer and less reactogenic as adjuvants than are at least some of the adjuvants currently approved for use in humans. The exemplar Bpc OMV adjuvant is derived from a bacterial strain, Bp82, that has a naturally-attenuated lipid A, which eliminates toxicity while preserving the full adjuvanticity of OMVs through Toll-like receptor (TLR) 4-dependent and -independent pathways. The results of our safety studies are described in greater detail below.

Safety evaluation in the MIMIC® System: Exemplar Bpc OMV were tested using the "Modular IMmune In vitro Construct" (MIMIC®) human cell culture system, developed by Sanofi Pasteur VaxDesign. The MIMIC® System characterizes potential human cell-cell interactions without the need to involve human subjects in a clinical trial. This allows for accurate pre-clinical testing and characterization of how proposed adjuvants, such as Bpc OMVs, might affect human immune cells. The MIMIC® System is based on the multidimensional interrogation of leukocytes. It can rapidly simulate a clinical trial, including the effect of an immunotherapy on human population subgroups where responses can be clustered into groups that capture genetic diversity and other important population characteristics, such as HLA haplotypes, age and gender. The MIMIC® System consists of isolated quiescent primary human cells placed into tissue-engineered constructs that are functionally and microenvironmentally equivalent to selected parts of the human immune system, specifically, peripheral tissue where the vaccine or the pathogen from the outside world initiates contact with human immune cells, and an artificial lymph node, where antigen-presenting cells from the immune system, the body's "sentinel" cells, engage the immune system's T and B cells and The MIMIC® System allows assessing human cell interactions from single human donors. This system also excels at the in vitro evaluation of human cellular toxicity of various pharmacologic compounds, including novel adjuvants such as Bpc OMVs. Studies of the exemplar Bpc OMVs in the MIMIC® System demonstrated that the cellular toxicity of the Bpc OMVs was comparable to other vaccines and vaccine adjuvants, such as the DTaP and yellow fever vaccines, and was not significantly different from no treatment, indicating that Bpc OMV are not toxic to human immune cells in a sophisticated culture system.

Figure 2:
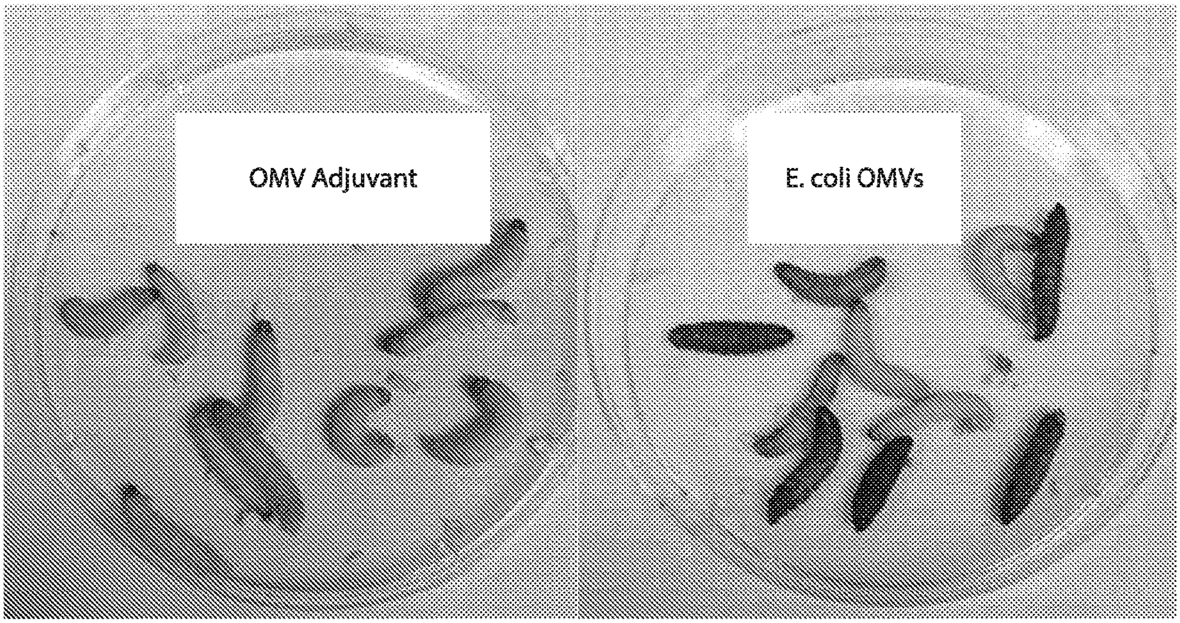
FIG. 2 presents photos of *G. mellonella* waxworm larvae that were injected with 2 μg of either *Burkholderia* outer membrane vesicles ("OMV Adjuvant") or *E. coli* outer membrane vesicles ("*E. coli* OMVs"). Larvae injected with OMV Adjuvant (left photo) remained motile, retained their natural color, and eventually progressed to pupation. *E. coli* OMVs (right hand photo) were toxic to 7 of 10 of the larvae, as indicated by lack of motility, black pigmentation, and death.

Safety evaluation in the Galleria melonella model: In addition to in vitro studies using the MIMIC® System, in vivo studies were performed in a model organism used for the evaluation of safety and toxicity. These in vivo studies used larvae of the wax moth Galleria melonella. This model has been used in multiple studies to assess, in particular, the toxicity of lipopolysaccharide ("LPS")-containing compounds, as these larvae are highly sensitive to LPS toxicity. Previous studies have demonstrated that the larvae of Galleria melonella are exquisitely sensitive to the toxic effects of various compounds, particularly *Salmonella* or *E. coli* LPS. When injected with even small amounts of LPS, G. melonella larvae rapidly succumb to the toxicity, physically curl into themselves, and die. FIG. 2 shows the results of studies in which *G. mellonella* waxworms (n=10) were injected with 2 μg BOMVs ("OMV adjuvant") (left picture) or *E. coli* OMVs (right picture) in 10 μl volume and monitored for 6 days. *E. coli* OMVs caused rapid toxicity in 7 of 10 waxworms by day 3 (shown) as indicated by absence of motility, black pigmentation, and death. In contrast, *G. mellonella* injected with OMV adjuvant (left picture) remained motile, retained their natural color, and eventually progressed to pupation. This indicates that Bpc OMVs do not contain toxic LPS or other compounds sufficient to kill a sensitive organism such as G. melonella.

Safety evaluation in the mouse model: We have extensive data on safety of the exemplar Bpc OMVs in mouse models of immunization. It is clear that Bpc OMV immunization does not affect body weight in BALB/c mice injected subcutaneously and in fact immunized mice gained weight and were thriving days after injection. Additionally, immunized mice show no injection site reactogenicity nor did they appear at any point to be moribund or lethargic. Grooming, eating, and drinking behaviors were normal and comparable to unimmunized mice. We have performed studies that mimic these in over 2000 mice, both via parenteral (subcutaneous, intradermal, and intramuscular) and mucosal (oral and intranasal) routes and have yet to note any reaction to Bpc OMVs. This demonstrates that in a small animal model used to assess safety, Bpc OMVs did not cause any adverse reactions, indicating that Bpc OMVs are an adjuvant safe for use in mammals.

Safety evaluation in a non-human primate (NHP) model: We have also assessed safety of exemplar Bpc OMVs in the NHP Rhesus Macaque model. In all, we have assessed safety in 14 animals and found that there was no injection site reactogenicity in any animal at any time after subcutaneous injection. To assess possible effects on organ function, blood chemistry from immunized NHP was monitored, and no change was seen in kidney or liver enzymes of NHP that received Bpc OMVs compared to those that were given vehicle control. In no instance was any adverse reaction noted following immunization with Bpc OMVs, demonstrating that this adjuvant is safe to use in non-human primates, and suggesting it is safe for use in another primate, humans.

Example 4

This Example shows that exemplar Bpc OMVs induce a potent immune response.

The hallmark of adjuvanticity is the ability of the adjuvant to induce a potent immune response. Ideally, the immune response will be diverse so as to combat multiple types of infectious organisms, from intracellular or extracellular bacteria to viruses and parasites. This diversity commonly includes the recruitment of innate immune cells such as neutrophils and monocytes to infected tissues; more important is induction of a diverse adaptive immune response including production of multiple antibody isotypes in addition to a potent multifunctional cytotoxic CD8+ T cell response and a multifunctional (Th1/Th17) helper CD4+ T cell outcome. We show that exemplar Bpc OMVs potentiate all of these outcomes in each of the in vitro and in vivo models discussed in Example 3, demonstrating that Bpc OMV ("BOMV") adjuvant will enhance the effectiveness of existing and new vaccines against a variety of diseases.

Innate immunity induction by Bpc OMVs: Here we discuss the ability of the exemplar BOMV adjuvant to induce an early innate immune response, focusing on each model system and on the recruitment of neutrophils and monocytes in addition to the activation of dendritic cells, which are subsequent inducers of adaptive immunity.

Figure 3:
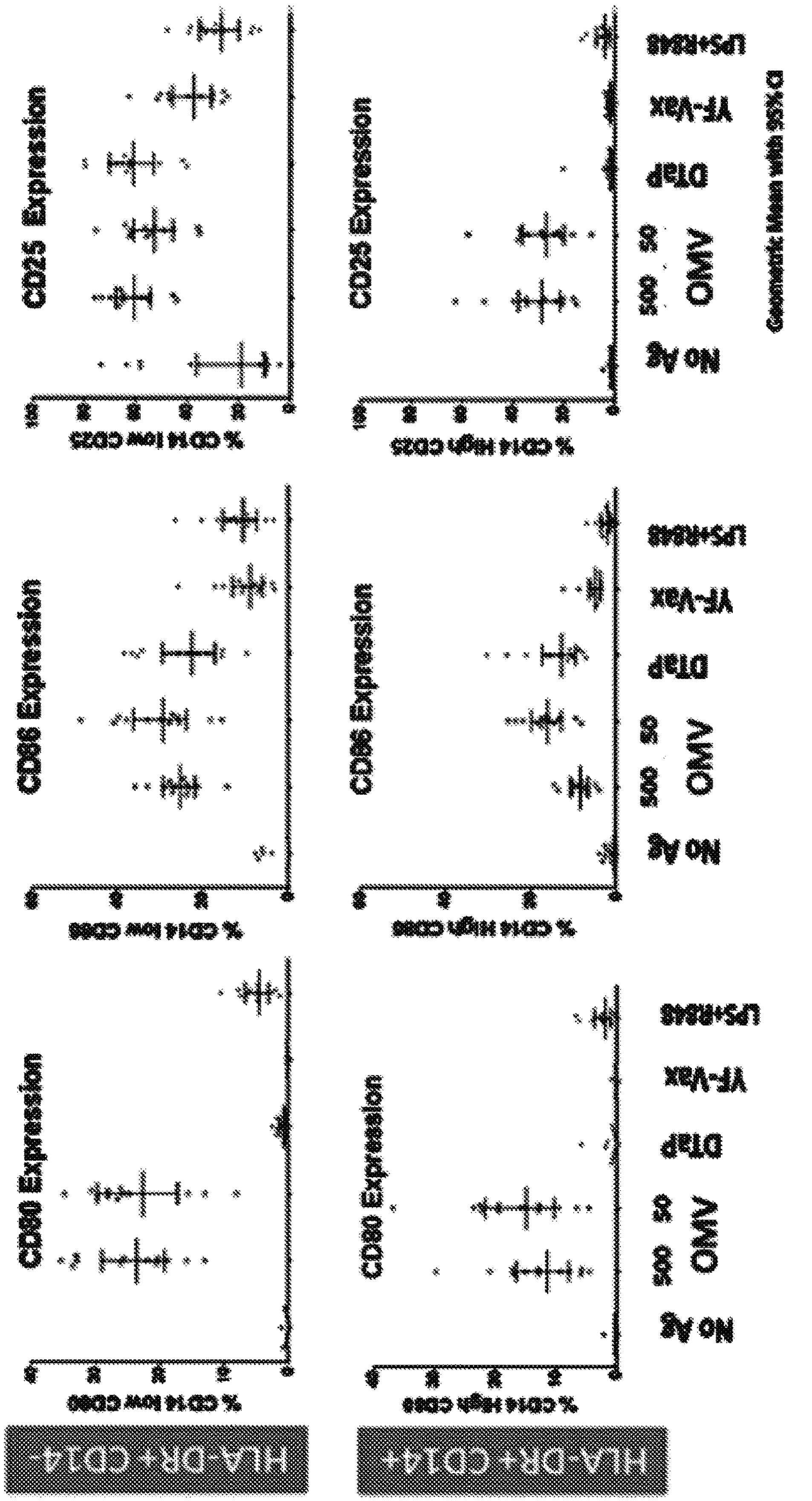
FIG. 3 compares the activation of antigen presenting cells ("APC") in the MIMIC® peripheral tissue equivalent ("PTE") system when treated with *Burkholderia pseudomallei* complex outer membrane vesicles ("BOMVs"), with DTaP, a commercially available vaccine against diphtheria, tetanus and pertussis, with YF-VAX®, a commercially available vaccine against yellow fever, or with toll like receptor ("TLR") agonists (lipopolysaccharide ("LPS")+R848). HLA-DR+CD14− cells=dendritic cells; HLA-DR+CD14+ cells=monocytes.

MIMIC® System (innate): The MIMIC® System is an excellent approach to testing how human cells would behave when exposed to Bpc OMVs and provides an idea of how human cells would likely behave following immunization. In this model, human blood monocytes are differentiated into human dendritic cells using three dimensional reverse transendothelial migration, a process reminiscent of the movement of cells from tissues into lymphatic vessels. This simulates the process of monocyte movement into peripheral tissues and is the most sophisticated in vitro approach available for differentiating human dendritic cells (DCs). The up-regulation of the activation/maturation markers on the DC and monocyte subsets were analyzed by flow cytometry. Using this system, we found that both mature DCs (CD14− HLADR+) and monocytes (CD14+HLADR+) from multiple human subjects expressed higher levels of the costimulatory molecules CD80 and CD86 when treated with Bpc OMVs when compared to DTaP, yellow fever vaccine (YF-VAX®), and LPS+R848 (FIG. 3). This is significant because the yellow fever vaccine is considered one of the most potent vaccine formulations available (a single dose provides lifelong immunity). Additionally, CD25, which is expressed on activated, mature DCs, is highest in Bpc OMV-treated cells.

Figure 4:
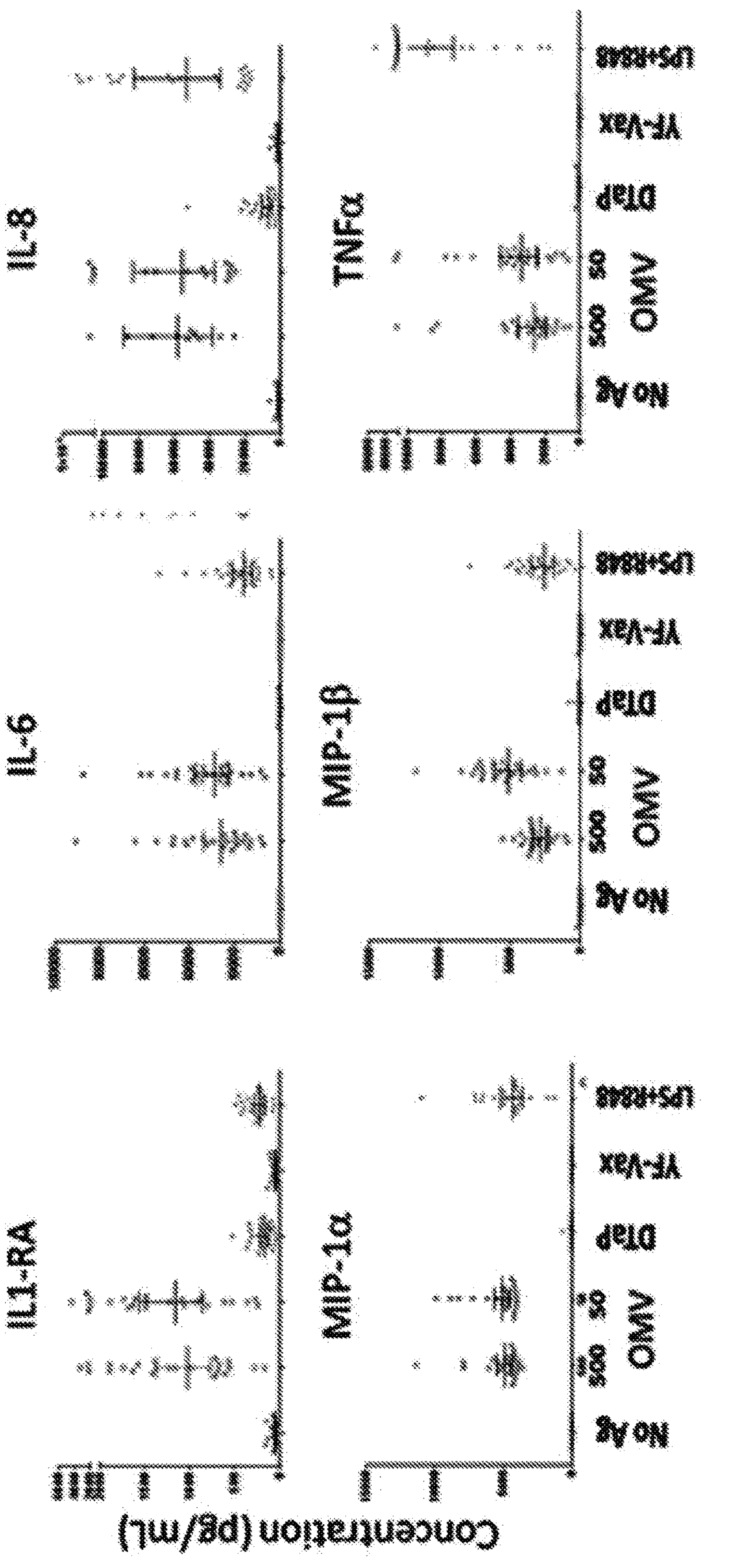
FIG. 4 presents graphs showing the induction of six chemokines/immune cytokines in the supernatant of dendritic cells treated in the MIMIC® peripheral tissue equivalent ("PTE") system with *Burkholderia pseudomallei* complex outer membrane vesicles ("OMVs"), with DTaP, a commercially available vaccine against diphtheria, tetanus and pertussis, with YF-VAX®, a commercially available vaccine against yellow fever, or with toll like receptor ("TLR") agonists (lipopolysaccharide ("LPS")+R848. Levels of chemokines/immune cytokines were evaluated by LUMINEX® bead assay.

The induction of chemokine/immune cytokines was also studied in this system. Culture supernatant of cells treated with BOMVs (OMV), commercial vaccines (DTaP or YF-Vax), or TLR agonists (LPS+R848) was taken and the induction of chemokine or immune cytokines were evaluated by LUMINEX® bead assay. As shown in FIG. 4, we found that the multiple inflammatory cytokines and chemokines are induced in human DCs after treatment with Bpc OMVs and again the levels are higher that what can be found in commercially available vaccines such as DTaP and yellow fever vaccine. Combined, these data demonstrate that exemplar Bpc OMVs can drive a potent innate immune response in the most important antigen presenting cell subset, DCs, and that this activation has the potential to initiate an even more potent adaptive immune response.

Mouse model (innate): We have investigated how the innate immune response is affected in mice following immunization or incubation with Bpc OMVs. We initially found that mouse bone marrow derived dendritic cells (BMDCs) behaved nearly identically to human DCs as described above. In particular, the costimulatory molecules CD40 and CD86 were significantly upregulated in BMDCs compared to heat killed bacteria. Additionally, major histocompatibility (MHC) class I and II were upregulated in BMDCs upon exposure to BOMVs at extremely low doses. This demonstrates that, in vitro in mouse cells, BOMVs can drive a response similar to what was observed in human cells, namely activation of the most effective antigen presenting cell type. This led us to explore the ability of BOMVs to affect innate immune changes in the in vivo mouse model.

Figure 5:
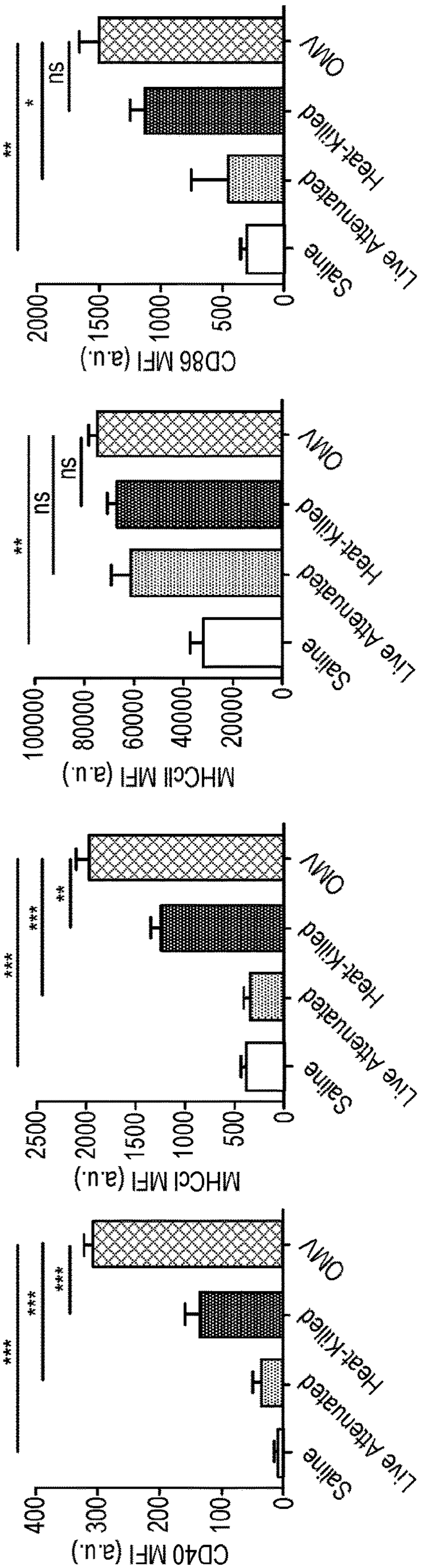
FIG. 5 presents graphs showing levels of surface markers on dendritic cells in mice intraperitoneally administered saline, live bacteria, heat-killed bacteria, or *Burkholderia pseudomallei* complex outer membrane vesicles. Six hours later, lavage of the peritoneal cavity ("PerC") was performed, and peritoneal exudate cells were recovered, stained for viability and surface marker expression analyzed by flow cytometry. The graphs present the mean flouresence intensity data mean+standard error of the mean ("SEM") for 3 mice per group. Legend: OMV=*Burkholderia pseudomallei* complex outer membrane vesicles, MFI=mean fluorescence intensity, ns=not significant, * $p>0.05$,  $p>0.01$, * $p>0.001$

C57BL/6 mice (n=3) were intra-peritoneally administered either with saline, 10 μg live bacteria, 10 μg heat-killed bacteria or 10 μg BOMVs. Six hours later mice were euthanized and a lavage of the peritoneal cavity ("PerC") was performed. Peritoneal exudate cells were recovered by centrifugation, stained for viability and surface marker expression and samples analyzed by flow cytometry. PerC dendritic cells (DCs) were gated as live (eF780−), Dump− (CD19, B220, CD3, NK1.1)(redFlour710), CD11b+ (BV510), FSc lo, CD11c+(PE-Cy7) and F4/80− (BV421). Median fluorescence intensity (MFI) for surface marker expression of CD40-PE, CD86-BV605, MHCcI-APC and MHCcII-PerCP-Cy5.5 was compared between groups. The results are shown in FIG. 5. The graphs present MFI data mean+standard error of the mean ("SEM") for 3 mice per group. One way ANOVA with tukey's post test was used to compare variances; ns not significant. * p>0.05,  p>0.01, * p>0.001. Our experiments demonstrated that injection of OMV adjuvant recapitulated the in vitro DC findings from both mice and humans where prominent DC activation markers (CD40, CD86, MHC I and MHCII) were all upregulated by OMV adjuvant.

Figure 6:
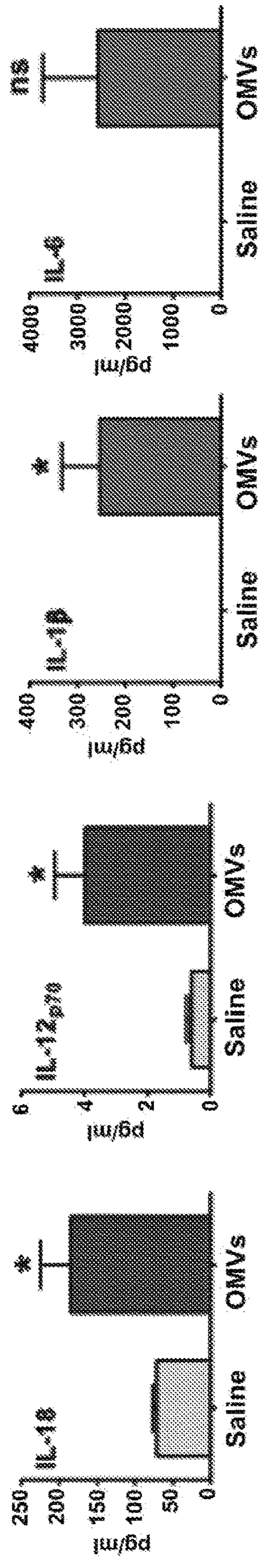
FIG. 6 presents graphs showing the levels of T cell polarizing cytokines in vivo in mice intraperitoneally administered either saline or 10 μg of *Burkholderia pseudomallei* complex outer membrane vesicles. Following peritoneal lavage, analyses of cytokines were performed. The graphs present the concentrations of cytokines IL-1B, IL-6, IL-12p70, and IL-18 mean+SEM for 3 mice per group.

Additionally, we found that T cell polarizing cytokines were induced in vivo by Bpc OMV injection, demonstrating that this adjuvant has the potential to shift the T cell response (discussed in depth below) toward a Th1/Th17 response when the adjuvant is used in a vaccine. In studies whose results are shown in the graphs presented in FIG. 6, C57BL/6 mice (n=3) were intra-peritoneally administered either with saline or 10 μg BOMVs (OMVs). Six hours later, the mice were euthanized and a lavage of the peritoneal cavity (PerC) performed. PerC washes were concentrated using 3 KDa centrifugal filters and multiplex analysis for cytokines and chemokines were performed on these samples. The graphs present concentrations of cytokines IL-1B, IL-6, IL-12p70 and IL-18 mean+SEM for 3 mice per group.

Figure 7:
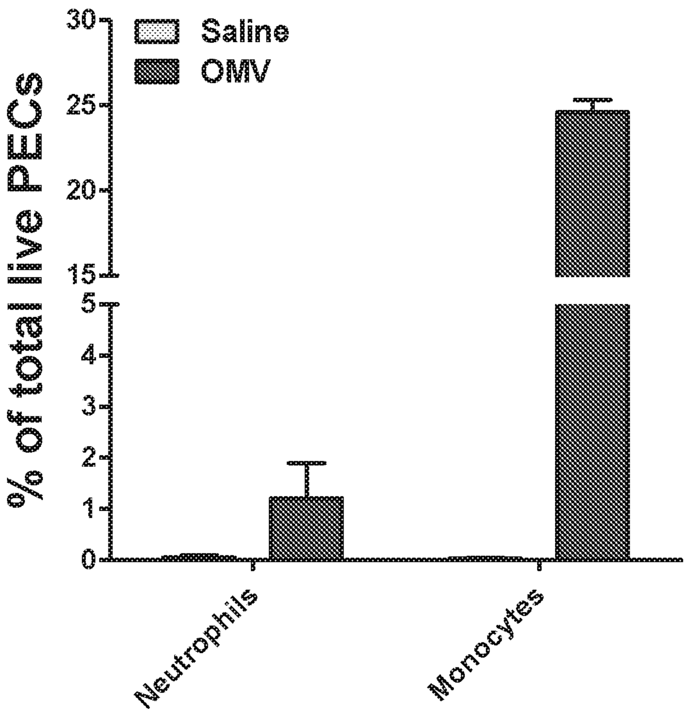
FIG. 7 presents a graph showing the percentages of neutrophils and monocytes of total live cells peritoneal exudate cells (PECs) recovered by peritoneal cavity lavage of mice that had been inter-peritoneally administered either saline or 10 μg Bp82-derived outer membrane vesicles ("OMV"), in mean+SEM for 3 mice per group. One way ANOVA with Tukey's post test was used to compare variances; *** $p>0.001$.

We next determined whether Bpc OMVs elicited other innate immune effects following immunization of mice. C57BL/6 mice (n=3) were intra-peritoneally administered either with saline or 10 μg Bp82 derived OMVs. Six hours later, the mice were euthanized and a lavage of the peritoneal cavity (PerC) performed. Peritoneal exudate cells (PECs) were recovered by centrifugation, stained for viability and surface marker expression and samples analyzed by flow cytometry. Neutrophils were gated as live (eF780−), CD11b+(BV510), CD11c− (PE-Cy7), F4/80− (PerCP-Cy5.5) and Gr-1hi (eF450). Monocytes were gated as live (eF780−), CD11b+(BV510), CD11c− (PE-Cy7), F4/80− (PerCP-Cy5.5) and Ly6C+(PE-CF594). The results are shown in FIG. 7. The graph presents the percentages of neutrophils and monocytes of total live cells mean+SEM for 3 mice per group. One way ANOVA with Tukey's post test was used to compare variances; * p>0.001. As shown in FIG. 7**, we found that Bpc OMV were capable of recruiting neutrophils and monocytes to the site of immunization. It is known that neutrophil recruitment is important for clearance of certain bacterial infections and this data implies that Bpc OMVs could be used as a therapeutic adjuvant, driving innate immune cell recruitment to sites of infection and possibly clearing ongoing infection.

NHP model (innate): The NHP model provides an opportunity to investigate how Bpc OMVs affect a more sophisticated mammalian model than mice. Like our other models, non-human primates show elevated neutrophil numbers, which then return to baseline 72 hours after immunization. This confirms that, in three distinct models assessing immunity, the innate immune response and in particular DC activation, demonstrated that Bpc OMVs were capable of initiating a potent innate response that can lead to a strong adaptive response. This response is discussed in detail below.

Adaptive immunity induction by Bpc OMVs: In this section, we show the ability of Bpc OMVs to induce a potent and diverse adaptive immune response, again focusing on each model system and on the T cell and antibody response in each MIMIC® System (adaptive).

Figure 8:
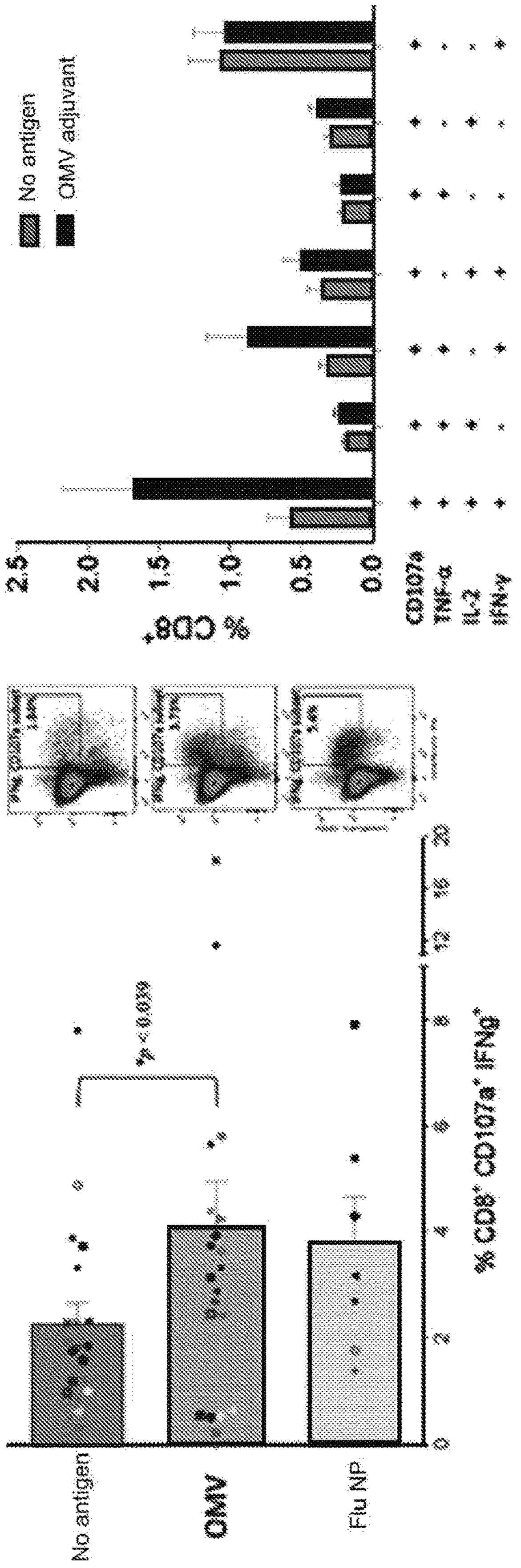
FIG. 8 shows the result of studies of CD8 T cell responses to *Burkholderia* outer membrane vesicles ("BOMV" or "OMV"). CD8 T cells were activated for 14 days with BOMV-primed APCs. The frequencies of CD107a+/cytokine+ T cells were analyzed by flow cytometry after challenge with cognate antigen loaded target cells. The left side graph shows that OMVs can stimulate CD8 T cell responses. This is significant because non-replicating vaccine platforms typically cannot achieve this. The middle of the figure presents a representative dot plot, and the right side represents multi-functional CD8 T cell responses analyzed by Boolean gating.

One of the great advantages the MIMIC® System provides is the ability to combine various immune cells from individual patients to reveal how different treatments could affect the outcome. At its most powerful, this model can resolve T cell differentiation and B cell antibody production from these human cells which is a powerful predictor of what would likely happen in a clinical trial. Because cells used in the MIMIC® System include antigen presenting cells and target cells (T cells or B cells or both), and because these cells share the same HLA type, the adaptive immune-driving interactions are likely to be similar to what could be expected following an injection of Bpc OMVs as an adjuvant in humans We initially assessed how exemplar Bpc OMVs would drive a cytotoxic CD8 T cell response in the MIMIC® system. Human DCs from individual patients were mixed with autologous, purified CD8 T cells and after two weeks, the activation state of the T cells was determined by CD107 expression and cytokine production. More specifically, CD8 T cells were activated for 14 days with BOMV-primed APCs. The frequencies of CD107a+/cytokine+ T cells were analyzed by flow cytometry after challenge with cognate antigen loaded target cells. The results are shown in FIG. 8. A representative dot plot is displayed in the middle and the multi-functional CD8 T cell responses analyzed by Boolean gating is on the right. OMV=BOMVs.

As shown in FIG. 8, Bpc OMVs were a powerful activator of CD8 T cells and, in fact, were as good as Flu nucleoprotein at activating CD8 T cells in this system. We also found that these CD8 T cells were more likely to be multifunctional, producing IFN-γ, IL-2 and TNF-α in the same cell as compared to no antigen. It is known that multifunctional T cells are correlated with greater vaccine efficacy or protection against infection and so this implies that Bpc OMVs have the capacity to drive protective CD8 T cell responses.

We next determined whether an exemplar Bpc OMVs dictate CD4 T helper responses in the MIMIC® System. Indeed, we found that Bpc OMVs preferentially drive a Th1 CD4 T cell response. More importantly, we also found that this Th1 response, like the CD8 response, was multifunctional, where T cells produced IFN-γ, IL-2 and TNF-α in the same cell, demonstrating that Bpc OMVs are excellent at inducing protective cellular immunity. Lastly, Bpc OMVs do not favor the induction of human regulatory T cells, showing that the immune response is unlikely to be tempered by these cells following immunization. Combined, these data show that Bpc OMVs are a potent inducer of cellular immunity and will excel at providing protection against both intracellular bacterial and viral infections when used as a vaccine adjuvant.

Figure 9:
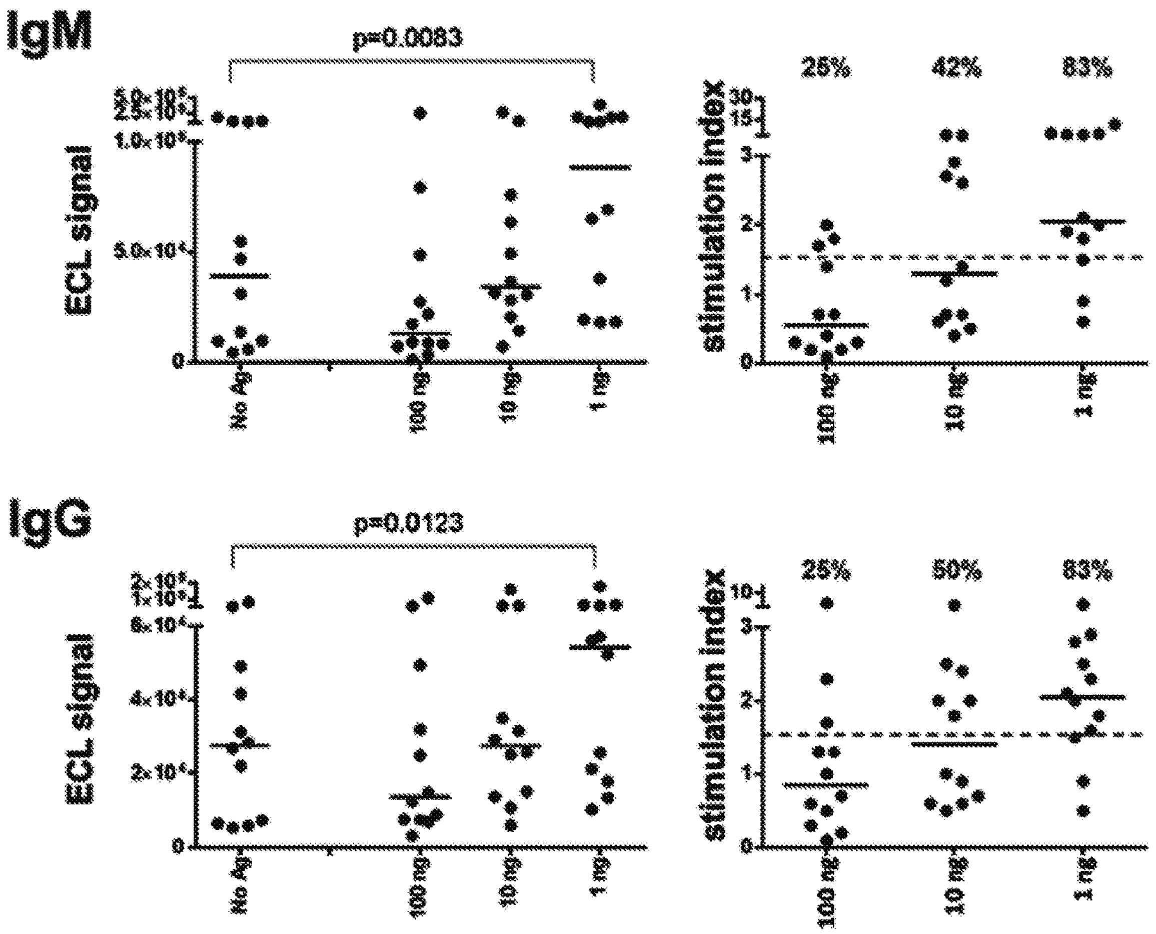
FIG. 9 shows the production of *Burkholderia* outer membrane vesicles (BOMV)-specific antibodies by naïve B cells and antigen-presenting cells (APCs) primed with BOMV and cultured with CD4 helper T cells for 14 days with B cell activating cytokines. The presence of antigen specific IgM or IgG was evaluated by Meso Scale Discovery (MSD). The production of Abs were also analyzed in stimulation index (ECL signal from Ag primed/ECL signal from No Ag primed), and the percentage of donors with an S.I.>1.5 are shown by the dotted line.

Lastly, we determined whether antibody production was provoked in the MIMIC® System using mixed B cells, T cells, and DCs from individual patients. Naïve B cells and APCs primed with BOMV were cultured with CD4 helper T cells for 14 days with B cell activating cytokines. The results are shown in the graphs presented as FIG. 9. The presence of antigen specific IgM or IgG was evaluated by Meso Scale Discovery (MSD). The production of Abs were also analyzed in stimulation index (ECL signal from Ag primed/ECL signal from No Ag primed), and the percentage of donors which has S.I.>1.5 are shown by the dotted lines in the graphs on the right side of the Figure. The presence of IgG (immunoglobulin isotype switched) implicates the strong immunogenic property of priming antigen. In this system, Bpc OMVs induced elevated IgM and IgG antigen-specific responses which were most heightened in the lower dose treatment groups. It should be noted that in the MIMIC® System, only the most potent formulations are able to induce antibody isotype switching.

These data demonstrate that Bpc OMVs are capable, in a sophisticated human cell-coculture system, of driving a combination of CD8, CD4, and humoral immune responses. Additionally, the CD4 T cell response was a more balanced Th1/Th17 response and both the CD8 and CD4 responses were multifunctional, with each cell simultaneously producing several cytokines. The results of these experiments predict that human responses would be expected to provide protection against multiple pathogenic organisms when used in vaccine preparations.

Figures 10A, 10B:
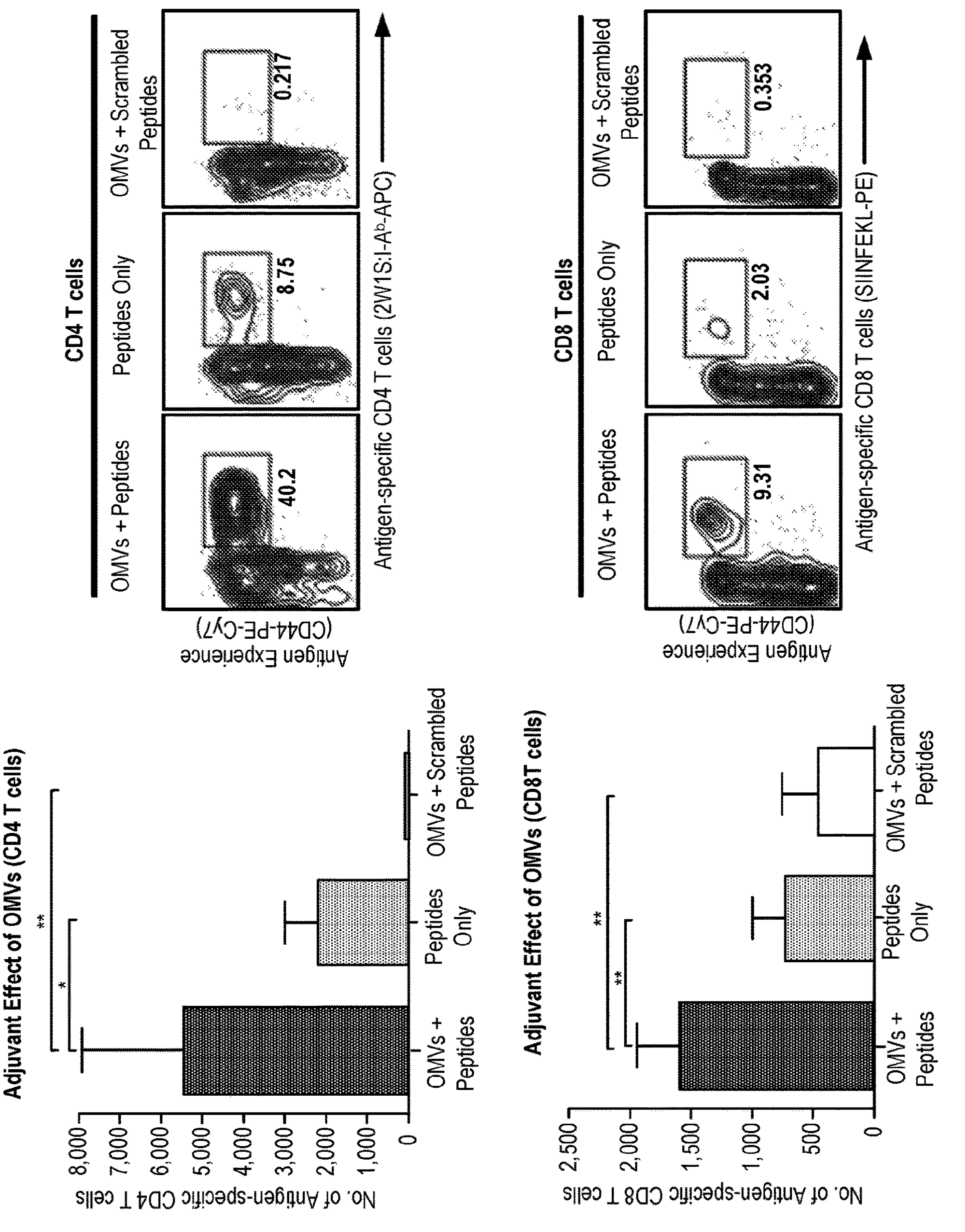
FIGS. 10A and 10B.

Mouse model (adaptive): Exemplar Bpc OMVs are excellent at driving adaptive immunity against co-administered antigens, in particular in conjunction with the DTaP vaccine and vaccine antigens. Initially, we used MHC class I and II tetramers to analyze the CD4 and CD8 T cell response to subcutaneous BOMV immunization. Notably, Bpc OMVs could induce a significantly greater endogenous antigen-specific CD4 and CD8 T cell responses. Mice were immunized with 200 μg of both CD4 (2W1S) and CD8 (SIINFEKL) model antigens. Two weeks later CD4 (FIG. 10A) and CD8 (FIG. 10B) T cell responses were assessed by FACS analysis using MHC-II and MHC-I tetramers respectively. Total antigen-specific T cell numbers were calculated and compared using One-Way ANOVA (n=4 per group *, p<0.05; **, p<0.01). Importantly, the CD8 T cells assayed produced more of the antimicrobial compounds perforin and granzyme, indicating these cells also had the potential of targeting and killing infected target cells and activating cellular immunity.

Figure 11:
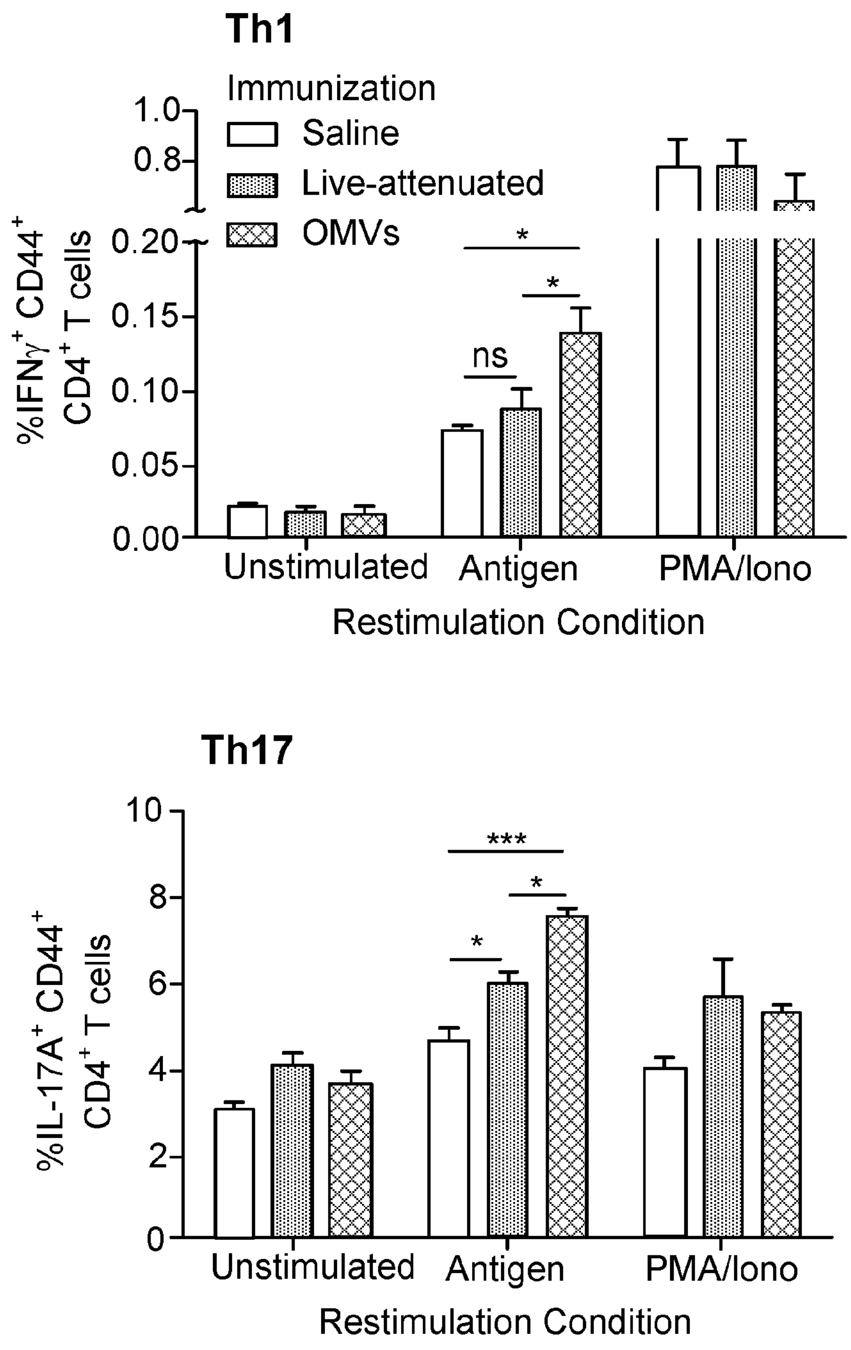
FIG. 11 presents graphs showing that *Burkholderia* outer membrane vesicles (OMV) drive balanced Th1 and Th17

FIG. 11 presents graphs of the TH1 and TH17 CD4 T cell response following a subcutaneous prime-boost regimen with 10 μg BOMV as an adjuvant. A significantly larger percentage of antigen-experienced CD4 T cells (gated as live, CD3+, CD4+, CD44+, Dump-) produced IFNγ and IL-17A, compared to mice vaccinated with live-attenuated bacteria following ex vivo restimulation with BOMV as an adjuvant. In accordance with the results we observed in the MIMIC® System, the CD4 T cell response to Bpc OMVs in mice was a balanced Th1/Th17 response, indicating that Bpc OMVs drives cellular immunity both in vitro and in vivo.

Example 5

This Example shows that exemplar Bpc OMVs enhance the potency of a current FDA-approved vaccine when co-administered with the vaccine.

We assessed the effect of co-administration of an exemplar Bpc OMV with an exemplar vaccine, DTaP vaccine (DAPTACEL®). FIG. 12 presents representative flow plots showing the results of studies in which DAPTACEL® was administered with Bpc OMV (left hand panel) or alone (right hand panel) using a model CD4 T cell antigen, 2W1S. The representative plots show increased T cell expansion in mice receiving OMV adjuvant compared to the vaccine alone (n=3-4). Numbers represent the percent antigen-specific CD4 T cells among all CD4 T cells. As shown in FIG. 12, while DAPTACEL® induced a potent antigen-specific endogenous CD4 T cell response, addition of Bpc OMVs enhanced this response.

We further tested the effect of Bpc OMV as an adjuvant in studies in which mice were immunized intradermally with ⅕th the human dose of DAPTACEL®, with or without 1 μg of Bp82 OMVs on day 0 and boosted on day 14. Serum was collected on day 28 via cardiac puncture. ELISAs were performed by coating high-binding plates with 0.5 μg/mL of each bacterial toxin or $5\times10^7$ CFUs of heat-killed *B. pertussis* per well in carbonate buffer, overnight at 37° C. A mouse IgG standard was included on each plate. Plates were incubated with serial dilutions of immunized serum, pre-immune serum/naïve serum. IgG responses were detected using a goat-anti-mouse total IgG-HRP secondary and developed using a TMB substrate. Plates were read at 450 nm and E.U./mL were calculated based off the Log EC50 of the standard curves on each plate. Groups were compared using a Student's t test (n=5-9 mice per group). The results are shown in FIG. 13. Importantly, when Bpc OMVs were co-administered with DAPTACEL® in mice, antibodies specific for Diphtheria toxoid, Tetanus toxoid, and Pertussis toxin were unaffected, indicating that Bpc OMV do not attenuate the normal response to DAPTACEL®. To the contrary, the antibody response against whole heat-killed Pertussis bacteria was enhanced when DAPTACEL® was administered with Bpc OMVs, indicating that this adjuvant has the potential to augment clearance of the bacteria when used with the existing, approved vaccine.

Collectively, the data in the mouse model of immunization closely follows the in vitro human MIMIC® System data. Both antigen-specific CD8 and CD4 T cells are driven to expand after immunization with BOMVs but more importantly, they elicit effector function, including the production of essential antimicrobial cytokines (IFN-γ and IL-17) as well as produce the cellular toxins perforin and granzyme. Bpc OMVs also drive a significant, and stable, antibody response. And, as discussed below, we also find that Bpc OMVs drive mucosal cellular and humoral immunity, providing confidence that this adjuvant possesses the capacity to regulate immunity at barrier surfaces Non-human primate (NHP) model (adaptive): We explored how Bpc OMVs affect the NHP model of immunization as well and find that, like the MIMIC® System and the mouse model, Bpc OMVs are excellent at driving both cellular immune responses, in which CD4 T cells are induced, and in which antibody level are heightened. The results of a study using Rhesus macaques are shown in FIG. 14. The macaques were immunized with OMV (animals IN71 and II81) or sham (animals DJ17 and HM73) three times, one month apart. Blood was collected 2 weeks after each immunization, and serum IgG was measured by ELISA.

The three models (the MIMIC® System, the mouse model, and the non-human primate model) closely follow one another, providing a high degree of confidence that Bpc OMVs will induce reproducible, sustained, and protective immune responses, when used as the adjuvant of choice in new vaccine formulations.

In this section, we demonstrated that Bpc OMVs excel at driving a multitude of immune responses, from potent and diverse cellular immunity to a vigorous humoral immune response. Further, we found that these responses were observable in three distinct models (in human cells in vitro, in mouse, and in NHP) lending support to the idea that Bpc OMVs drive an exceptionally diverse immune response.

Example 6

This Example shows that exemplar Bpc OMVs enhance the potency of a vaccine when co-administered.

The most essential aspect of development of a new adjuvant for use in the next generation of vaccines is to define whether it can enhance the vaccine's protection against infection. Ideally, the adjuvant would be used in conjunction with an immunogenic antigen derived from a pathogen and the immune response against that antigen would be protective. We tested this possibility using the exemplar Bpc OMVs in a well-established lethal, oral model of *Salmonella* infection in mice.

Mice were immunized orally with $3\times10^8$ CFUs of heat-killed S. *Typhimurium* SL1344 ("HK SL1344" or "HKS") with or without 10 μg of Bp82 OMVs on day 0 and 14. Mice were challenged orally with $1\times10^5$ CFUs of wild-type S. *Typhimurium* SL1344 on day 28. Weight was monitored daily, and mice were humanely euthanized when they lost >20% of their prechallenge weight. Mouse weight was statistically analyzed using multiple Student t tests, comparing each group per day (n=6-9 mice per group; *, p<0.05; , p<0.01; *, p<0.001). Mouse survival was analyzed using a Mantel-Cox test (n=6-9 mice per group). As shown in FIG. 15, mice immunized with HKS alone rapidly lost body weight and quickly succumbed to the infection. In contrast, when Bpc OMVs were included in the immunization, 80% of the mice survived and, in fact, they mostly maintained original body weight over the course of the study. In our previous work with this infection model, we could only achieve 60% survival at best, even using as an adjuvant Freund's complete adjuvant, indicating that the Bpc OMVs were superior even to Freund's complete adjuvant as an adjuvant, while causing no toxicity or observable side effects.

These results demonstrate that Bpc OMVs are highly protective in a lethal enteric infection model. This data, combined with the data from the Examples set forth above, indicate that Bpc OMVs have the potential to be useful adjuvants in a multitude of future vaccine preparations and could provide enhanced protection against a wide variety of pathogens.

Example 7

This Example shows that exemplar Bpc OMVs are immunogenic both parentally and mucosally.

One concern with the current stable of vaccine adjuvants is that they do not always induce protective immunity across different tissues. For example, parenterally injected alum does not induce significant levels of mucosal antibodies and is poor at driving mucosal cellular immunity. While mucosal immunization would likely be most effective, alum is not administered mucosally for safety reasons. In fact, there are currently no adjuvants approved for human mucosal administration (oral/intranasal/intravaginal). This creates something of a paradox, as most pathogens enter via mucosal routes, so the ability to protect at these sites would be desirable. As such, the ability of an adjuvant to either 1) drive mucosal and systemic immunity when injected parenterally or 2) be safe enough to drive systemic and mucosal immunity when administered mucosally would be ideal. The Examples above presented data that Bpc OMVs are highly immunogenic when administered parenterally and also show that oral (mucosal) administration of Bpc OMVs in conjunction with HKS is protective against a lethal *Salmonella* infection. These two data sets show that Bpc OMVs excel at both inducing systemic and mucosal immunity.

To further investigate this, mice were intranasally immunized with Bpc OMVs and assessed for antigen-specific IgA responses. Microtiter plates were coated with 500 ng/well of purified Bpc OMV adjuvant or *E. coli* OMVs. A significantly higher IgA response was found in mice given Bpc OMVs plus antigen, compared to antigen alone, demonstrating that mucosal-associated, humoral immunity is induced when Bpc OMVs are administered mucosally (See, FIGS. 16A and B). Notably, Bpc OMV adjuvant-immunized mice did not induce *E. coli* OMV cross-reactive antibodies, demonstrating the specificity of the Bpc OMV adjuvant. This shows that mucosal administration of Bpc OMVs plus an antigen induces potent, and protective, mucosal immunity. Importantly, no adverse reactions to mucosal administration of Bpc OMVs were noted, indicating that Bpc OMVs are safe when used as an adjuvant in mucosal administration. Combined, the data satisfy both above conditions where systemic and mucosal protective immunity can be induced via parenteral or mucosal routes, safely and efficiently, demonstrating that Bpc OMVs have the potential to combat a multitude of pathogens and to protect multiple sites through which pathogens can enter.

Example 8

This Example shows that exemplar Bpc OMVs do not induce self-specific antibodies that would prevent use in multiple vaccines.

While certain adjuvants, such as alum, do not induce self-specific antibodies and thus are not subject to pre-existing immunity affecting booster immunizations, certain larger molecule adjuvants (MPL, cholera toxin) succumb to lowered efficacy due to the existence of antibodies directed against the vaccine, which blocks their effectiveness. Because Bpc OMVs are just such a large molecule adjuvant, we investigated whether pre-existing immunity could alter the efficiency of Bpc OMVs as an adjuvant when used to boost immune responses. Initially, we determined whether T cell responses were affected by pre-existing anti-Bpc OMVs antibodies. Mice were twice immunized subcutaneously with 1 μg of the exemplar Bpc OMVs (Bp82 OMVs) on days 0 and 7 to induce anti-Bpc OMVs antibodies, and then were immunized with 1 μg of the exemplar Bpc OMVs, plus 200 ng of a T cell antigen, 2W1S peptide, on days 14 and 21 to induce antigen-specific T cell responses. Control mice were given PBS on days 0 and 7, and then immunized on days 14 and 21 with the same immunization as in the experimental group. On day 28, serum was harvested for ELISAs and draining lymph nodes and spleens were harvested for T cell analysis. ELISAs were performed in duplicate by coating high-binding plates with 1 μg per well of Bp82 OMVs overnight at 4° C. A mouse IgG standard was included on each plate. Plates were incubated with serial dilutions of immunized serum and IgG responses were detected using a goat-anti-mouse total IgGHRP secondary and developed using a TMB substrate. Plates were read at 450 nm and E.U./mL were calculated based off the Log EC50 of the standard curves on each plate. Groups were compared using One-Way ANOVA (n=2 per group; *, p<0.05; **, p<0.001). The number of antigen-specific CD4 T cells were determined by flow cytometry using MHC-II tetramers (I-Ab:2W1S-APC). T cell numbers were compared statistically using a Student t test (n=2 mice per group). As shown in FIG. 17**, anti-Bpc OMVs antibodies were induced to a high level; however, these antibodies did not affect the ability for the Bpc OMVs to elicit a potent, antigen-specific CD4 T cell response to the co-administered antigen.

As noted above, Bpc OMVs induce significantly more antibodies against whole heat-killed Pertussis bacteria (see, FIG. 13), even though anti-Bpc OMV antibodies are produced following immunization, as shown in FIG. 16A. Combined, these data demonstrate that pre-existing anti-Bpc OMVs antibodies do not affect subsequent cellular or humoral immunity against co-administered antigen. It is possible that this can be attributed to the rapid innate effect of Bpc OMVs on DCs shown in a prior Example. Because of this, anti-Bpc OMVs antibodies may respond too late against Bpc OMVs to affect their ability to initiate a secondary response to co-administered antigen. This shows that Bpc OMVs can be used as an adjuvant in multiple vaccines without affecting efficacy following booster immunizations.

Example 9

This Example summarizes the results shown in the preceding Examples.

The data presented here demonstrate that Bpc OMVs have the potential to be used as an adjuvant in both existing and new vaccines, and even alongside currently used adjuvants, such as alum. An ideal adjuvant should induce both potent cellular and humoral immune responses and Bpc OMVs excel at both of these, including induction of a diverse Th1/Th17 and activated cytotoxic T cell response. Because Bpc OMVs are so broadly immunostimulatory, they have the potential to serve as the adjuvant of choice against a multitude of pathogens that infect via different routes or survive in normally immune privileged niches. One example of this is *Salmonella* bacteria, which has evolved to reside intracellularly in macrophages, avoiding the humoral immune response. Bpc OMVs as an adjuvant can enhance protection against this infection, demonstrating its potency against these types of infections. Despite being a potent immune activator, Bpc OMVs are also safe to administer via traditional parenteral routes or mucosal routes, causing no observable side effects or reactogenicity. New adjuvants are badly needed to induce a wide variety of immune responses against pathogenic threats. Bpc OMVs fit this need and have the potential to shift the paradigm of how current and future vaccines are adjuvanted.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. An immunogenic composition, said composition comprising (a) a plurality of outer membrane vesicles (OMVs) derived from one or more organisms of the *B. pseudomallei* complex ("Bpc") and, (b) a non-*Burkholderia* immunogen from *Clostridium botulinum, C. perfringens, Chlamydia psittaci, Coxiella burnetii, Ricinus communis, Rickettsia prowazekii, Vibrio cholerae, Cryptosportidium parvum, Yersinia pestis, Francisella tularensis*, a *Brucella* species, *E. coli* O157:H7, Variola major virus, Machupo virus, or a member of the Togaviridae (collectively, "the pathogenic organisms").

2. The immunogenic composition of claim 1, wherein said one or more organisms of the Bpc are *Burkholderia pseudomallei, B. mallei, B. oklahomensis, B. thailandensis, B. humptydooensis*, or *Burkholderia* spp. Clades A, B, or C.

3. The immunogenic composition of claim 1, wherein said one or more organisms of the Bpc are *B. pseudomallei* or *B. mallei.*

4. The immunogenic composition of claim 1, wherein said organisms of the Bpc have attenuated pathogenicity compared to wild-type members of said Bpc species or Glade.

5. The immunogenic composition of claim 4 wherein said attenuated pathogenicity of said Bpc organisms is due to deletion or truncation of purM.

6. The immunogenic composition of claim 5, wherein said Bpc species is *B. pseudomallei.*

7. The immunogenic composition of claim 4, wherein said attenuated pathogenicity of said Bpc organisms is due to deletion or disruption of tonB, of hcp1, or of both of said Bpc organisms.

8. The immunogenic composition of claim 1, further comprising an aluminum salt, saponin, oil-in-water, or CpG nucleotide adjuvant.

9. The immunogenic composition of claim 1, further comprising a pharmaceutically acceptable excipient.

10. The immunogenic composition of claim 1, wherein said immunogen is a killed or attenuated member of the pathogenic organisms or is derived from a member of the pathogenic organisms.

11. The immunogenic composition of claim 10, wherein said killed or attenuated member of the pathogenic organisms or member of the pathogenic organisms from which said immunogen is derived is a bacterium.

12. The immunogenic composition of claim 11, wherein said bacterium is *Clostridium botulinum, C. perfringens, Chlamydia psittaci, Coxiella burnetii, Ricinus communis, Rickettsia prowazekii, Vibrio cholerae, Cryptosportidium parvum, Yersinia pestis, Francisella tularensis*, a *Brucella*, or *E. coli* O157:H7.

13. The immunogenic composition of claim 10, wherein said killed or attenuated member of the pathogenic organisms or member of the pathogenic organisms from which said immunogen is derived is a virus.

14. The immunogenic composition of claim 13, wherein said virus is Variola major virus, Machupo virus, Chikungunya virus, Venezuelan equine encephalitis virus, eastern equine encephalitis virus, or western equine encephalitis virus.

15. The immunogenic composition of claim 1, wherein said immunogen is encapsulated within said OMVs.

16. The immunogenic composition of claim 1, wherein said immunogenic composition further comprises a stabilizer, a buffer, or both a stabilizer and a buffer.

17. A method of increasing a subject's immune response to a non-*Burkholderia* immunogen, said method comprising co-administering to said subject (a) a plurality of outer membrane vesicles (OMVs) derived from one or more organisms of the *B. pseudomallei* complex ("Bpc") and, (b) a non-*Burkholderia* immunogen from *Clostridium botulinum, C. perfringens, Chlamydia psittaci, Coxiella burnetii, Ricinus communis, Rickettsia prowazekii, Vibrio cholerae, Cryptosportidium parvum, Yersinia pestis, Francisella tularensis*, a *Brucella* species, *E. coli* O157:H7, Variola major virus, Machupo virus, or a member of the Togaviridae (collectively, "the pathogenic organisms").

18. The method of claim 17, wherein said Bpc is of the group consisting of *Burkholderia pseudomallei, B. mallei, B. oklahomensis, B. thailandensis, B. humptydooensis, Bur-*

*kholderia* spp. Clade A, *Burkholderia* spp. Clade B, and *Burkholderia* spp. Clade C (collectively, "*B. pseudomallei* complex" or "Bpc").

19. The method of claim 17, wherein said immunogen and said effective amount of said OMVs are mixed to form a single composition prior to said co-administration.

20. The method of claim 17, wherein said composition is lyophilized.

21. The method of claim 20, wherein said lyophilized composition is reconstituted prior to said co-administration.

22. The method of claim 17, wherein said composition further comprises a stabilizer, a buffer, or both a stabilizer and a buffer.

23. The method of claim 17, wherein said subject is a primate, an equine, a bovine, an ovine, a porcine, a canine, a feline, or a camelid.

24. The method of claim 23, wherein said primate is a human.

25. The method of claim 17, wherein said OMVs are of *B. pseudomallei* or *B. mallei*.

26. The method of claim 17, wherein said organisms of said Bpc have attenuated pathogenicity compared to wild-type organisms of said Bpc.

27. The method of claim 26, wherein said organisms of said Bpc are organisms of *Burkholderia pseudomallei, B. mallei, B. oklahomensis, B. thailandensis, B. humptydooensis, Burkholderia* spp. Clade A, *Burkholderia* spp. Clade B, or *Burkholderia* spp. Clade C, and have attenuated pathogenicity compared to wild type *Burkholderia pseudomallei, B. mallei, B. oklahomensis, B. thailandensis, B. humptydooensis, Burkholderia* spp. Clade A, *Burkholderia* spp. Clade B, or *Burkholderia* spp. Clade C, respectively.

28. The method of claim 26, wherein said attenuated pathogenicity is due to deletion or truncation of purM or of deletion or disruption of tonB, of hcp1, or of both.

29. The method of claim 26, wherein said *B. pseudomallei* is *B. pseudomallei* Bp82.

30. The method of claim 17, wherein said immunogen is a killed or attenuated member of the pathogenic organisms or is derived from one of the pathogenic organisms.

31. The method of claim 30, wherein said killed or attenuated member of the pathogenic organisms or member of the pathogenic organisms from which said immunogen is derived is a bacterium.

32. The method of claim 31, wherein said bacterium is *Clostridium botulinum, C. perfringens, Chlamydia psittaci, Coxiella burnetii, Ricinus communis, Rickettsia prowazekii, Vibrio cholerae, Cryptosportidium parvum, Yersinia pestis, Francisella tularensis*, a *Brucella* species, or *E. coli* O157:H7.

33. The method of claim 30, wherein said killed or attenuated member of the pathogenic organisms or member of the pathogenic organisms from which said immunogen is derived is a virus.

34. The method of claim 33, wherein said virus is Variola major virus, Machupo virus, Chikungunya virus, Venezuelan equine encephalitis virus, eastern equine encephalitis virus, or western equine encephalitis virus.

35. The method of claim 17, wherein said co-administration is intravenous, intraperitoneal, intramuscular, intracavity, subcutaneous, intradermal, intranasal, or transdermal.

* * * * *